United States Patent
London et al.

(10) Patent No.: US 7,291,469 B2
(45) Date of Patent: Nov. 6, 2007

(54) MUTANT MET AND USES THEREFOR

(75) Inventors: Cheryl A. London, Woodland, CA (US); Albert Liao, Sacramento, CA (US)

(73) Assignee: The Regents of the University of California, Oakland, CA (US)

(*) Notice: Subject to any disclaimer, the term of this patent is extended or adjusted under 35 U.S.C. 154(b) by 48 days.

(21) Appl. No.: 11/208,414

(22) Filed: Aug. 18, 2005

(65) Prior Publication Data

US 2006/0057619 A1 Mar. 16, 2006

Related U.S. Application Data

(60) Provisional application No. 60/602,778, filed on Aug. 18, 2004.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search .................. None
See application file for complete search history.

(56) References Cited

OTHER PUBLICATIONS

Tacher et al. (J. of Heredity, vol. 96, No. 7, pp. 812-816, 2005).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Nastiuk et al (Prostates, vol. 40, No. 3, pp. 172-177, 1999).*

* cited by examiner

*Primary Examiner*—Jeanine A. Goldberg
(74) *Attorney, Agent, or Firm*—Townsend and Townsend and Crew LLP

(57) ABSTRACT

The present invention provides compositions and methods for detecting mutations in the proto-oncogene Met.

6 Claims, 8 Drawing Sheets

Figure 1

```
Alignment of Canine MET wild type and mutant (G1630A) nucleotide sequences
WT Met        1   ATGAAGGCTC CTGCTGTGCT TGCACCTGGC ATCCTTGTGC TTCTGTTTAC
MUTANT MET    1   ATGAAGGCTC CTGCTGTGCT TGCACCTGGC ATCCTTGTGC TTCTGTTTAC WT Met       51   CTTGGTGCAG AAGAGCTATG GGGAGTGCAA AGAGGCACTA GTAAAGTCTG
MUTANT MET   51   CTTGGTGCAG AAGAGCTATG GGGAGTGCAA AGAGGCACTA GTAAAGTCTG WT Met      101   AGATGAATGT GAACATGAAG TATCAGCTTC CCAACTTCAC TGCCGAAACA
MUTANT MET  101   AGATGAATGT GAACATGAAG TATCAGCTTC CCAACTTCAC TGCCGAAACA WT Met      151   CCCATCCAGA ATGTTGTTTT ACACAAGCAT CATATTTACC TTGGTGCAGT
MUTANT MET  151   CCCATCCAGA ATGTTGTTTT ACACAAGCAT CATATTTACC TTGGTGCAGT WT Met      201   TAACTATATT TACGTTTTAA ATGACAAAGA CCTTCAGAAG GTTGCTGAGT
MUTANT MET  201   TAACTATATT TACGTTTTAA ATGACAAAGA CCTTCAGAAG GTTGCTGAGT WT Met      251   ACAAGACTGG GCCCGTGCTG GAACACCCAG ATTGTTCCCC ATGTCAGGAC
MUTANT MET  251   ACAAGACTGG GCCCGTGCTG GAACACCCAG ATTGTTCCCC ATGTCAGGAC WT Met      301   TGCAGCCACA AAGCCAATTT ATCAGGTGGT GTTTGGGAAG ATAACATCAA
MUTANT MET  301   TGCAGCCACA AAGCCAATTT ATCAGGTGGT GTTTGGGAAG ATAACATCAA WT Met      351   CATGGCTCTG CTTGTTGACA CATACTACGA TGACCAACTC ATTAGCTGTG
MUTANT MET  351   CATGGCTCTG CTTGTTGACA CATACTACGA TGACCAACTC ATTAGCTGTG WT Met      401   GCAGTGTCCA CAGAGGGACC TGCCAGCGAC ATATCCTTCC ACCCAGCAAT
MUTANT MET  401   GCAGTGTCCA CAGAGGGACC TGCCAGCGAC ATATCCTTCC ACCCAGCAAT WT Met      451   ATTGCTGACA TACAGTCGGA AGTGCATTGC ATGTACTCCT CACAGGCAGA
MUTANT MET  451   ATTGCTGACA TACAGTCGGA AGTGCATTGC ATGTACTCCT CACAGGCAGA WT Met      501   CGAAGAGCCC AGCCAGTGCC CTGACTGTGT GGTGAGTGCT CTAGGAACCA
MUTANT MET  501   CGAAGAGCCC AGCCAGTGCC CTGACTGTGT GGTGAGTGCT CTAGGAACCA WT Met      551   AAGTCCTGAT ATCAGAAAAG GACCGGTTCA TCAACTTCTT CGTAGGCAAT
MUTANT MET  551   AAGTCCTGAT ATCAGAAAAG GACCGGTTCA TCAACTTCTT CGTAGGCAAT WT Met      601   ACCATAAATT CCTCGGACCA TCCAGATCAT TCATTGCATT CGATATCGGT
MUTANT MET  601   ACCATAAATT CCTCGGACCA TCCAGATCAT TCATTGCATT CGATATCGGT WT Met      651   GAGAAGGCTA AAGGAAACGC AAGATGGGTT CAAGTTTTTG ACAGACCAGT
MUTANT MET  651   GAGAAGGCTA AAGGAAACGC AAGATGGGTT CAAGTTTTTG ACAGACCAGT WT Met      701   CTTACATTGA TGTTCTACCG GAGTTCAGAG ACTCCTACCC CATTAAATAT
MUTANT MET  701   CTTACATTGA TGTTCTACCG GAGTTCAGAG ACTCCTACCC CATTAAATAT WT Met      751   GTCCACGCCT TTGAAAGCAA CCACTTTATT TACTTTTTGA CAGTCCAGCG
MUTANT MET  751   GTCCACGCCT TTGAAAGCAA CCACTTTATT TACTTTTTGA CAGTCCAGCG WT Met      801   AGAAACTCTA GATGCTCAGA CTTTTCACAC GAGAATAATC AGGTTCTGTT
MUTANT MET  801   AGAAACTCTA GATGCTCAGA CTTTTCACAC GAGAATAATC AGGTTCTGTT WT Met      851   CTGTAGACTC TGGATTGCAT TCCTACATGG AAATGCCTCT GGAGTGTATT
MUTANT MET  851   CTGTAGACTC TGGATTGCAT TCCTACATGG AAATGCCTCT GGAGTGTATT WT Met      901   CTCACGGAAA AGAGAAGAAA GAGATCCACA AGGGAGGAAG TGTTTAATAT
MUTANT MET  901   CTCACGGAAA AGAGAAGAAA GAGATCCACA AGGGAGGAAG TGTTTAATAT

951   TCTCCAAGCT GCATATGTCA GTAAGCCTGG GGCCCATCTC GCTAAACAAA
```

| | | |
|---|---|---|
| WT Met | | |
| MUTANT MET | 951 | TCTCCAAGCT GCATATGTCA GTAAGCCTGG GGCCCATCTC GCTAAACAAA |
| WT Met | 1001 | TAGGTGCCAA CCTGAATGAT GACATTCTCT ATGGAGTGTT CGCACAAAGC |
| MUTANT MET | 1001 | TAGGTGCCAA CCTGAATGAT GACATTCTCT ATGGAGTGTT CGCACAAAGC |
| WT Met | 1051 | AAGCCAGATT CTGCTGAACC AATGAATCGC TCTGCCGTCT GTGCGTTCCC |
| MUTANT MET | 1051 | AAGCCAGATT CTGCTGAACC AATGAATCGC TCTGCCGTCT GTGCGTTCCC |
| WT Met | 1101 | TATCAAATAT GTCAATGAAT TCTTCAACAA GATCGTCAAC AAAAACAATG |
| MUTANT MET | 1101 | TATCAAATAT GTCAATGAAT TCTTCAACAA GATCGTCAAC AAAAACAATG |
| WT Met | 1151 | TGAGATGTCT TCAGCACTTT TATGGACCCA ACCACGAACA CTGCTTTAAT |
| MUTANT MET | 1151 | TGAGATGTCT TCAGCACTTT TATGGACCCA ACCACGAACA CTGCTTTAAT |
| WT Met | 1201 | AGGACACTTT TGAGAAATTC ATCGGGCTGT GAAGCGCGCA ATGATGAATA |
| MUTANT MET | 1201 | AGGACACTTT TGAGAAATTC ATCGGGCTGT GAAGCGCGCA ATGATGAATA |
| WT Met | 1251 | TCGAACGGAG TTCACTACAG CTTTGCAGCG CGTTGACTTA TTCATGGGCC |
| MUTANT MET | 1251 | TCGAACGGAG TTCACTACAG CTTTGCAGCG CGTTGACTTA TTCATGGGCC |
| WT Met | 1301 | AGTTCAACCA AGTCCTCTTA ACGTCTATAT CCACCTTCAT CAAAGGAGAC |
| MUTANT MET | 1301 | AGTTCAACCA AGTCCTCTTA ACGTCTATAT CCACCTTCAT CAAAGGAGAC |
| WT Met | 1351 | CTCACCATTG CTAATCTTGG GACGTCCGAG GGTCGCTTCA TGCAGGTCGT |
| MUTANT MET | 1351 | CTCACCATTG CTAATCTTGG GACGTCCGAG GGTCGCTTCA TGCAGGTCGT |
| WT Met | 1401 | GGTTTCTCGA TCAGGATTGT CGACCCCTCA CGTGAACTTC CGCCTGGACT |
| MUTANT MET | 1401 | GGTTTCTCGA TCAGGATTGT CGACCCCTCA CGTGAACTTC CGCCTGGACT |
| WT Met | 1451 | CCCACCCCGT GTCTCCAGAA GCAATTGTGG AGCACCCACT AAACCAAAAC |
| MUTANT MET | 1451 | CCCACCCCGT GTCTCCAGAA GCAATTGTGG AGCACCCACT AAACCAAAAC |
| WT Met | 1501 | GGCTACACAC TCGTTGTCAC TGGGAAGAAG ATCACCAGGA TCCCACTGAA |
| MUTANT MET | 1501 | GGCTACACAC TCGTTGTCAC TGGGAAGAAG ATCACCAGGA TCCCACTGAA |
| WT Met | 1551 | TGGCTTAGGC TGTGAGCATT TTCAGTCCTG CAGTCAGTGT CTCTCCGCCC |
| MUTANT MET | 1551 | TGGCTTAGGC TGTGAGCATT TTCAGTCCTG CAGTCAGTGT CTCTCCGCCC |
| WT Met | 1601 | CTCCCTTTGT GCAGTGTGGC TGGTGCCACG ATAGATGTGT GCACCTGGAG |
| MUTANT MET | 1601 | CTCCCTTTGT GCAGTGTGGC TGGTGCCACA ATAGATGTGT GCACCTGGAG |
| WT Met | 1651 | GAATGTCCCA CTGGAGCGTG GACTCAGGAG GTCTGTCTGC CTGCAATCTA |
| MUTANT MET | 1651 | GAATGTCCCA CTGGAGCGTG GACTCAGGAG GTCTGTCTGC CTGCAATCTA |
| WT Met | 1701 | TGAGGTTTTC CCAACTAGTG CACCCCTGGA AGGAGGGACA GTGCTGACTG |
| MUTANT MET | 1701 | TGAGGTTTTC CCAACTAGTG CACCCCTGGA AGGAGGGACA GTGCTGACTG |
| WT Met | 1751 | TATGTGGCTG GGACTTCGGA TTCAGGAGGA ATAATAAATT TGATTTAAAG |
| MUTANT MET | 1751 | TATGTGGCTG GGACTTCGGA TTCAGGAGGA ATAATAAATT TGATTTAAAG |
| WT Met | 1801 | AAAACCAAAG TTTTCCTTGG AAATGAGAGC TGCACCTTGA CCTTAAGTGA |
| MUTANT MET | 1801 | AAAACCAAAG TTTTCCTTGG AAATGAGAGC TGCACCTTGA CCTTAAGTGA |
| WT Met | 1851 | GAGCACAACA AATATGCTGA ATGCACAGT TGGCCCTGCA GTGAACGAGC |
| MUTANT MET | 1851 | GAGCACAACA AATATGCTGA ATGCACAGT TGGCCCTGCA GTGAACGAGC |
| WT Met | 1901 | ATTTCAATAT ATCCATAATT ATTTCAAATG GTCGAGGGAC AGCACAATAT |
| MUTANT MET | 1901 | ATTTCAATAT ATCCATAATT ATTTCAAATG GTCGAGGGAC AGCACAATAT |
| WT Met | 1951 | AGTACATTTT CGTATGTGGA TCCTATTATA ACAAGTATTT CTCCAAGTTA |

| | | | | | |
|---|---|---|---|---|---|
| MUTANT MET | 1951 | AGTACATTTT | CGTATGTGGA | TCCTATTATA | ACAAGTATTT CTCCAAGTTA |
| WT Met | 2001 | TGGTCCCAAG | AATGGTGGCA | CCTTGCTCAC | TTTAACTGGA AAATACCTCA |
| MUTANT MET | 2001 | TGGTCCCAAG | AATGGTGGCA | CCTTGCTCAC | TTTAACTGGA AAATACCTCA |
| WT Met | 2051 | ACAGTGGGAA | TTCTAGACAC | ATTTCAATGG | GTGGAAAAAC ATGTACTTTA |
| MUTANT MET | 2051 | ACAGTGGGAA | TTCTAGACAC | ATTTCAATGG | GTGGAAAAAC ATGTACTTTA |
| WT Met | 2101 | AAAAGTGTGT | CAGATAGTAT | TCTCGAATGT | TATACCCCAG CTCAAGCCAC |
| MUTANT MET | 2101 | AAAAGTGTGT | CAGATAGTAT | TCTCGAATGT | TATACCCCAG CTCAAGCCAC |
| WT Met | 2151 | TGCAACTGAG | TTTCCTATTA | AATTGAAAAT | TGACCTAGCC AACCGAGAGA |
| MUTANT MET | 2151 | TGCAACTGAG | TTTCCTATTA | AATTGAAAAT | TGACCTAGCC AACCGAGAGA |
| WT Met | 2201 | TGAACAGCTT | CAGTTACCAG | GAAGACCCCA | TTGTCTATGC AATTCATCCA |
| MUTANT MET | 2201 | TGAACAGCTT | CAGTTACCAG | GAAGACCCCA | TTGTCTATGC AATTCATCCA |
| WT Met | 2251 | ACGAAATCTT | TTATTAGTGG | TGGGAGCACA | ATAACAGCTG TTGGAAAAAA |
| MUTANT MET | 2251 | ACGAAATCTT | TTATTAGTGG | TGGGAGCACA | ATAACAGCTG TTGGAAAAAA |
| WT Met | 2301 | CCTGAATTCA | GTGAGTGTCC | TGAGGATGGT | AATAGATGTC CATGAAACAA |
| MUTANT MET | 2301 | CCTGAATTCA | GTGAGTGTCC | TGAGGATGGT | AATAGATGTC CATGAAACAA |
| WT Met | 2351 | GAAGGAACTT | TACAGTGGCA | TGTCAACATC | GCTCTAATTC AGAGATAATC |
| MUTANT MET | 2351 | GAAGGAACTT | TACAGTGGCA | TGTCAACATC | GCTCTAATTC AGAGATAATC |
| WT Met | 2401 | TGTTGTACGA | CTCCTTCACT | GCAACAGCTG | AATCTGCAAC TCCCTCTGAA |
| MUTANT MET | 2401 | TGTTGTACGA | CTCCTTCACT | GCAACAGCTG | AATCTGCAAC TCCCTCTGAA |
| WT Met | 2451 | AACCAAAGCC | TTTTTCATGT | TAGATGGGAT | CCATTCCAAA TACTTTGATC |
| MUTANT MET | 2451 | AACCAAAGCC | TTTTTCATGT | TAGATGGGAT | CCATTCCAAA TACTTTGATC |
| WT Met | 2501 | TCATTTATGT | ACATAATCCT | GTGTTTAAGC | CTTTTGAAAA GCCAGTGATG |
| MUTANT MET | 2501 | TCATTTATGT | ACATAATCCT | GTGTTTAAGC | CTTTTGAAAA GCCAGTGATG |
| WT Met | 2551 | ATCTCAATAG | GCAATGAAAA | TGTACTGGAA | ATTAAGGGAA ATGATATTGA |
| MUTANT MET | 2551 | ATCTCAATAG | GCAATGAAAA | TGTACTGGAA | ATTAAGGGAA ATGATATTGA |
| WT Met | 2601 | CCCTGAAGCA | GTTAAAGGCG | AAGTGTTAAA | AGTTGGAAAT AAGAGCTGTG |
| MUTANT MET | 2601 | CCCTGAAGCA | GTTAAAGGCG | AAGTGTTAAA | AGTTGGAAAT AAGAGCTGTG |
| WT Met | 2651 | AGACTATCTA | CTCAGATTCT | AAAGCCGTTT | TATGCAAGGT CCCCAATGAC |
| MUTANT MET | 2651 | AGACTATCTA | CTCAGATTCT | AAAGCCGTTT | TATGCAAGGT CCCCAATGAC |
| WT Met | 2701 | CTGCTGAAAT | TGAACAACGA | GCTAAATATA | GAGTGGAAGC AAGCAGTTTC |
| MUTANT MET | 2701 | CTGCTGAAAT | TGAACAACGA | GCTAAATATA | GAGTGGAAGC AAGCAGTTTC |
| WT Met | 2751 | TTCAACCGTC | CTTGGAAAAG | TAATAGTTCA | ACCAGATCAG AATTTCACAG |
| MUTANT MET | 2751 | TTCAACCGTC | CTTGGAAAAG | TAATAGTTCA | ACCAGATCAG AATTTCACAG |
| WT Met | 2801 | GATTGATTGC | TGGTGTTATC | TCAATATCAA | CAATAGTCTT ATTATTACTC |
| MUTANT MET | 2801 | GATTGATTGC | TGGTGTTATC | TCAATATCAA | CAATAGTCTT ATTATTACTC |
| WT Met | 2851 | GGACTTTTCC | TGTGGCTGAA | AAGGAAAAAG | CAAATTAAAG ATCTGGGCAG |
| MUTANT MET | 2851 | GGACTTTTCC | TGTGGCTGAA | AAGGAAAAAG | CAAATTAAAG ATCTGGGCAG |
| WT Met | 2901 | TGAATTAGTT | CGCTATGATG | CAAGAGTACA | CACTCCTCAT TTGGATAGGC |
| MUTANT MET | 2901 | TGAATTAGTT | CGCTATGATG | CAAGAGTACA | CACTCCTCAT TTGGATAGGC |
| WT Met | 2951 | TTGTAAGTGC | CCGAAGTGTA | AGCCCAACTA | CAGAAATGGT TTCAAATGAA |
| MUTANT MET | 2951 | TTGTAAGTGC | CCGAAGTGTA | AGCCCAACTA | CAGAAATGGT TTCAAATGAA |

| | | |
|---|---|---|
| WT Met | 3001 | TCTGTAGACT ACCGAGCTAC TTTTCCAGAA GACCAGTTTC CTAATTCATC |
| MUTANT MET | 3001 | TCTGTAGACT ACCGAGCTAC TTTTCCAGAA GACCAGTTTC CTAATTCATC |
| WT Met | 3051 | TCAGAATGGA TCATGCAGAC AAGTACAATA TCCTCTGACG GACCTGTCCC |
| MUTANT MET | 3051 | TCAGAATGGA TCATGCAGAC AAGTACAATA TCCTCTGACG GACCTGTCCC |
| WT Met | 3101 | CCATGCTTAC TAGTGGGGAC TCTGATATAT CCAGTCCATT ATTGCAAAAT |
| MUTANT MET | 3101 | CCATGCTTAC TAGTGGGGAC TCTGATATAT CCAGTCCATT ATTGCAAAAT |
| WT Met | 3151 | ACTGTCCACA TTGACCTCAG TGCTCTAAAT CCAGAGCTGG TGCAGGCAGT |
| MUTANT MET | 3151 | ACTGTCCACA TTGACCTCAG TGCTCTAAAT CCAGAGCTGG TGCAGGCAGT |
| WT Met | 3201 | CCAGCATGTA GTGATTGGGC CCAGTAGCCT GATTGTGCAT TTCAATGAAG |
| MUTANT MET | 3201 | CCAGCATGTA GTGATTGGGC CCAGTAGCCT GATTGTGCAT TTCAATGAAG |
| WT Met | 3251 | TCATAGGAAG AGGACATTTT GGGTGTGTAT ACCATGGGAC TTTGTTGGAC |
| MUTANT MET | 3251 | TCATAGGAAG AGGACATTTT GGGTGTGTAT ACCATGGGAC TTTGTTGGAC |
| WT Met | 3301 | AATGACGACA AAAAAATTCA CTGTGCTGTG AAATCCCTGA ATAGAATCAC |
| MUTANT MET | 3301 | AATGACGACA AAAAAATTCA CTGTGCTGTG AAATCCCTGA ATAGAATCAC |
| WT Met | 3351 | TGACATAGGA GAAGTTTCCC AGTTTCTGAC CGAGGGAATC ATCATGAAAG |
| MUTANT MET | 3351 | TGACATAGGA GAAGTTTCCC AGTTTCTGAC CGAGGGAATC ATCATGAAAG |
| WT Met | 3401 | ATTTTAGTCA TCCAAACGTA CTCTCACTCT TGGGAATCTG CCTTCGAAGT |
| MUTANT MET | 3401 | ATTTTAGTCA TCCAAACGTA CTCTCACTCT TGGGAATCTG CCTTCGAAGT |
| WT Met | 3451 | GAGGGGTCTC CACTGGTGGT CCTACCATAC ATGAAACATG GAGATCTTCG |
| MUTANT MET | 3451 | GAGGGGTCTC CACTGGTGGT CCTACCATAC ATGAAACATG GAGATCTTCG |
| WT Met | 3501 | AAATTTCATT AGAAATGAGA CTCATAACCC AACTGTAAAA GATCTTATTG |
| MUTANT MET | 3501 | AAATTTCATT AGAAATGAGA CTCATAACCC AACTGTAAAA GATCTTATTG |
| WT Met | 3551 | GCTTTGGTCT TCAAGTAGCC AAAGGCATGA AATATCTTGC AAGCAAAAAG |
| MUTANT MET | 3551 | GCTTTGGTCT TCAAGTAGCC AAAGGCATGA AATATCTTGC AAGCAAAAAG |
| WT Met | 3601 | TTTGTCCACA GAGACTTGGC TGCAAGAAAC TGTATGCTGG ATGAAAAATT |
| MUTANT MET | 3601 | TTTGTCCACA GAGACTTGGC TGCAAGAAAC TGTATGCTGG ATGAAAAATT |
| WT Met | 3651 | CACTGTCAAG GTTGCTGATT TTGGTCTTGC CAGAGACATG TATGATAAAG |
| MUTANT MET | 3651 | CACTGTCAAG GTTGCTGATT TTGGTCTTGC CAGAGACATG TATGATAAAG |
| WT Met | 3701 | AATACTACAG CGTACACAAC AAAACAGGCG CCAAACTACC AGTGAAGTGG |
| MUTANT MET | 3701 | AATACTACAG CGTACACAAC AAAACAGGCG CCAAACTACC AGTGAAGTGG |
| WT Met | 3751 | ATGGCTTTAG AAAGTCTGCA AACTCAGAAG TTTACCACCA AGTCAGATGT |
| MUTANT MET | 3751 | ATGGCTTTAG AAAGTCTGCA AACTCAGAAG TTTACCACCA AGTCAGATGT |
| WT Met | 3801 | GTGGTCCTTT GGCGTGCTCC TCTGGGAACT GATGACAAGA GGAGCACCAC |
| MUTANT MET | 3801 | GTGGTCCTTT GGCGTGCTCC TCTGGGAACT GATGACAAGA GGAGCACCAC |
| WT Met | 3851 | CTTATCCTGA CGTCAACACC TTTGATATAA CAGTTTACTT GTTGCAAGGC |
| MUTANT MET | 3851 | CTTATCCTGA CGTCAACACC TTTGATATAA CAGTTTACTT GTTGCAAGGC |
| WT Met | 3901 | AGAAGGCTCC TGCAACCCGA ATACTGCCCA GATCCCTTAT ACGAAGTGAT |
| MUTANT MET | 3901 | AGAAGGCTCC TGCAACCCGA ATACTGCCCA GATCCCTTAT ACGAAGTGAT |
| WT Met | 3951 | GCTAAAATGC TGGCACCCTA GAGCTGAACT GCGCCCATCT TTTTCTGAAC |
| MUTANT MET | 3951 | GCTAAAATGC TGGCACCCTA GAGCTGAACT GCGCCCATCT TTTTCTGAAC |

```
WT Met       4001  TGGTCTCCAG GATATCAGCA ATATTCTCTA CTTTCATTGG GGAGCACTAT
MUTANT MET   4001  TGGTCTCCAG GATATCAGCA ATATTCTCTA CTTTCATTGG GGAGCACTAT

WT Met       4051  GTCCATGTGA ACGCCACTTA TGTGAATGTC AAATGTGTTG CTCCATACCC
MUTANT MET   4051  GTCCATGTGA ACGCCACTTA TGTGAATGTC AAATGTGTTG CTCCATACCC

WT Met       4101  TTCTCTCTTG TCATCACAAG ATAACATTGA TGGCGAGGGG GACACATGA
MUTANT MET   4101  TTCTCTCTTG TCATCACAAG ATAACATTGA TGGCGAGGGG GACACATGA
```

Figure 2
Alignment of Canine c-MET wild-type and mutant (D544N) amino acid sequences

```
WT Met          1   MKAPAVLAPG ILVLLFTLVQ KSYGECKEAL VKSEMNVNMK YQLPNFTAET
MUTANT MET      1   MKAPAVLAPG ILVLLFTLVQ KSYGECKEAL VKSEMNVNMK YQLPNFTAET

WT Met         51   PIQNVVLHKH HIYLGAVNYI YVLNDKDLQK VAEYKTGPVL EHPDCSPCQD
MUTANT MET     51   PIQNVVLHKH HIYLGAVNYI YVLNDKDLQK VAEYKTGPVL EHPDCSPCQD

WT Met        101   CSHKANLSGG VWEDNINMAL LVDTYYDDQL ISCGSVHRGT CQRHILPPSN
MUTANT MET    101   CSHKANLSGG VWEDNINMAL LVDTYYDDQL ISCGSVHRGT CQRHILPPSN

WT Met        151   IADIQSEVHC MYSSQADEEP SQCPDCVVSA LGTKVLISEK DRFINFFVGN
MUTANT MET    151   IADIQSEVHC MYSSQADEEP SQCPDCVVSA LGTKVLISEK DRFINFFVGN

WT Met        201   TINSSDHPDH SLHSISVRRL KETQDGFKFL TDQSYIDVLP EFRDSYPIKY
MUTANT MET    201   TINSSDHPDH SLHSISVRRL KETQDGFKFL TDQSYIDVLP EFRDSYPIKY

WT Met        251   VHAFESNHFI YFLTVQRETL DAQTFHTRII RFCSVDSGLH SYMEMPLECI
MUTANT MET    251   VHAFESNHFI YFLTVQRETL DAQTFHTRII RFCSVDSGLH SYMEMPLECI

WT Met        301   LTEKRRKRST REEVFNILQA AYVSKPGAHL AKQIGANLND DILYGVFAQS
MUTANT MET    301   LTEKRRKRST REEVFNILQA AYVSKPGAHL AKQIGANLND DILYGVFAQS

WT Met        351   KPDSAEPMNR SAVCAFPIKY VNEFFNKIVN KNNVRCLQHF YGPNHEHCFN
MUTANT MET    351   KPDSAEPMNR SAVCAFPIKY VNEFFNKIVN KNNVRCLQHF YGPNHEHCFN

WT Met        401   RTLLRNSSGC EARNDEYRTE FTTALQRVDL FMGQFNQVLL TSISTFIKGD
MUTANT MET    401   RTLLRNSSGC EARNDEYRTE FTTALQRVDL FMGQFNQVLL TSISTFIKGD

WT Met        451   LTIANLGTSE GRFMQVVVSR SGLSTPHVNF RLDSHPVSPE AIVEHPLNQN
MUTANT MET    451   LTIANLGTSE GRFMQVVVSR SGLSTPHVNF RLDSHPVSPE AIVEHPLNQN

WT Met        501   GYTLVVTGKK ITRIPLNGLG CEHFQSCSQC LSAPPFVQCG WCHDRCVHLE
MUTANT MET    501   GYTLVVTGKK ITRIPLNGLG CEHFQSCSQC LSAPPFVQCG WCHNRCVHLE

WT Met        551   ECPTGAWTQE VCLPAIYEVF PTSAPLEGGT VLTVCGWDFG FRRNNKFDLK
MUTANT MET    551   ECPTGAWTQE VCLPAIYEVF PTSAPLEGGT VLTVCGWDFG FRRNNKFDLK

WT Met        601   KTKVFLGNES CTLTLSESTT NMLKCTVGPA VNEHFNISII ISNGRGTAQY
MUTANT MET    601   KTKVFLGNES CTLTLSESTT NMLKCTVGPA VNEHFNISII ISNGRGTAQY

WT Met        651   STFSYVDPII TSISPSYGPK NGGTLLTLTG KYLNSGNSRH ISMGGKTCTL
MUTANT MET    651   STFSYVDPII TSISPSYGPK NGGTLLTLTG KYLNSGNSRH ISMGGKTCTL

WT Met        701   KSVSDSILEC YTPAQATATE FPIKLKIDLA NREMNSFSYQ EDPIVYAIHP
MUTANT MET    701   KSVSDSILEC YTPAQATATE FPIKLKIDLA NREMNSFSYQ EDPIVYAIHP

WT Met        751   TKSFISGGST ITAVGKNLNS VSVLRMVIDV HETRRNFTVA CQHRSNSEII
MUTANT MET    751   TKSFISGGST ITAVGKNLNS VSVLRMVIDV HETRRNFTVA CQHRSNSEII

WT Met        801   CCTTPSLQQL NLQLPLKTKA FFMLDGIHSK YFDLIYVHNP VFKPFEKPVM
MUTANT MET    801   CCTTPSLQQL NLQLPLKTKA FFMLDGIHSK YFDLIYVHNP VFKPFEKPVM

WT Met        851   ISIGNENVLE IKGNDIDPEA VKGEVLKVGN KSCETIYSDS KAVLCKVPND
MUTANT MET    851   ISIGNENVLE IKGNDIDPEA VKGEVLKVGN KSCETIYSDS KAVLCKVPND

WT Met        901   LLKLNNELNI EWKQAVSSTV LGKVIVQPDQ NFTGLIAGVI SISTIVLLLL
MUTANT MET    901   LLKLNNELNI EWKQAVSSTV LGKVIVQPDQ NFTGLIAGVI SISTIVLLLL

WT Met        951   GLFLWLKRKK QIKDLGSELV RYDARVHTPH LDRLVSARSV SPTTEMVSNE
MUTANT MET    951   GLFLWLKRKK QIKDLGSELV RYDARVHTPH LDRLVSARSV SPTTEMVSNE
```

```
WT Met         1001   SVDYRATFPE  DQFPNSSQNG  SCRQVQYPLT  DLSPMLTSGD  SDISSPLLQN
MUTANT MET     1001   SVDYRATFPE  DQFPNSSQNG  SCRQVQYPLT  DLSPMLTSGD  SDISSPLLQN

WT Met         1051   TVHIDLSALN  PELVQAVQHV  VIGPSSLIVH  FNEVIGRGHF  GCVYHGTLLD
MUTANT MET     1051   TVHIDLSALN  PELVQAVQHV  VIGPSSLIVH  FNEVIGRGHF  GCVYHGTLLD

WT Met         1101   NDDKKIHCAV  KSLNRITDIG  EVSQFLTEGI  IMKDFSHPNV  LSLLGICLRS
MUTANT MET     1101   NDDKKIHCAV  KSLNRITDIG  EVSQFLTEGI  IMKDFSHPNV  LSLLGICLRS

WT Met         1151   EGSPLVVLPY  MKHGDLRNFI  RNETHNPTVK  DLIGFGLQVA  KGMKYLASKK
MUTANT MET     1151   EGSPLVVLPY  MKHGDLRNFI  RNETHNPTVK  DLIGFGLQVA  KGMKYLASKK

WT Met         1201   FVHRDLAARN  CMLDEKFTVK  VADFGLARDM  YDKEYYSVHN  KTGAKLPVKW
MUTANT MET     1201   FVHRDLAARN  CMLDEKFTVK  VADFGLARDM  YDKEYYSVHN  KTGAKLPVKW

WT Met         1251   MALESLQTQK  FTTKSDVWSF  GVLLWELMTR  GAPPYPDVNT  FDITVYLLQG
MUTANT MET     1251   MALESLQTQK  FTTKSDVWSF  GVLLWELMTR  GAPPYPDVNT  FDITVYLLQG

WT Met         1301   RRLLQPEYCP  DPLYEVMLKC  WHPRAELRPS  FSELVSRISA  IFSTFIGEHY
MUTANT MET     1301   RRLLQPEYCP  DPLYEVMLKC  WHPRAELRPS  FSELVSRISA  IFSTFIGEHY

WT Met         1351   VHVNATYVNV  KCVAPYPSLL  SSQDNIDGEG  DT*
MUTANT MET     1351   VHVNATYVNV  KCVAPYPSLL  SSQDNIDGEG  DT*
```

Figure 3
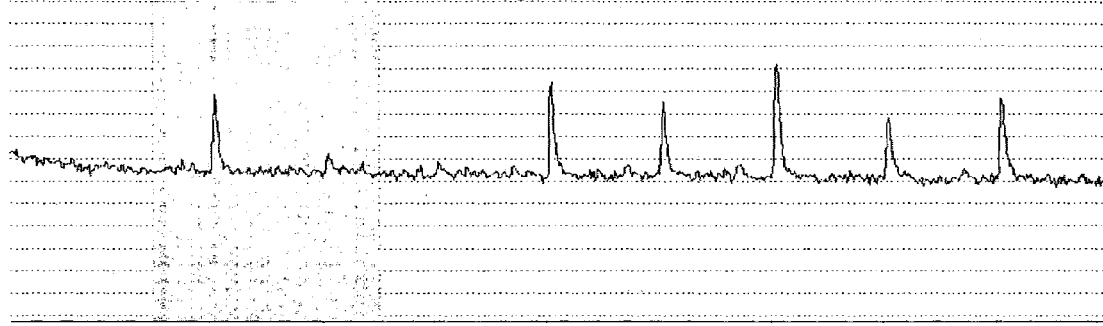
Figure 3A. Pyrosequencing data from a homozygous unaffected individual. The shaded area indicates the position of interest.
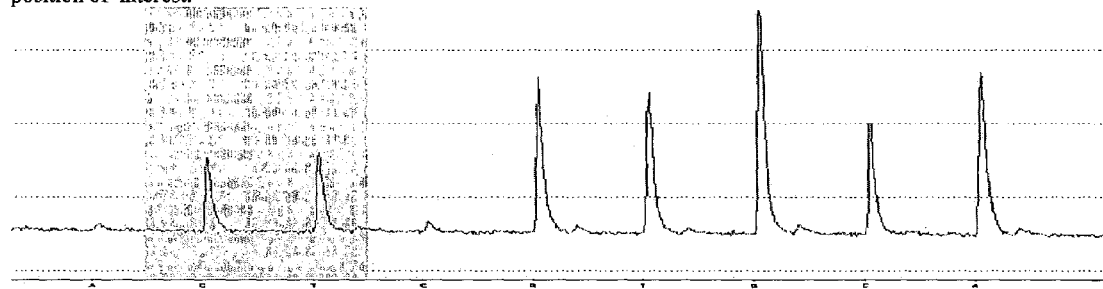
Figure 3B. Pyrosequencing data from a heterozygous individual. The shaded area indicates the position of interest.
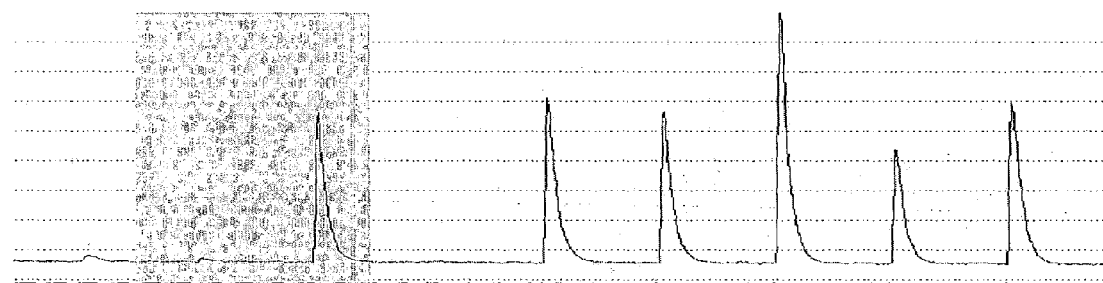
Figure 3C. Pyrosequencing data from a homozygous affected individual. The shaded area indicates the position of interest.

SEQUENCE LISTING

<160> NUMBER OF SEQ ID NOS: 16

<210> SEQ ID NO 1
<211> LENGTH: 4149
<212> TYPE: DNA
<213> ORGANISM: Canis familiaris
<220> FEATURE:
<223> OTHER INFORMATION: canine Met (hepatocyte growth factor (HGF), scatter factor) G966S (G2896A) mutant

<400> SEQUENCE: 1

```
atgaaggctc ctgctgtgct tgcacctggc atccttgtgc ttctgtttac cttggtgcag    60
aagagctatg gggagtgcaa agaggcacta gtaaagtctg agatgaatgt gaacatgaag   120
tatcagcttc ccaacttcac tgccgaaaca cccatccaga atgttgtttt acacaagcat   180
catatttacc ttggtgcagt taactatatt tacgttttaa tgacaaaga ccttcagaag   240
gttgctgagt acaagactgg gcccgtgctg aacacccag attgttcccc atgtcaggac   300
tgcagccaca agccaatttt atcaggtggt gtttgggaag ataacatcaa catggctctg   360
cttgttgaca catactacga tgaccaactc attagctgtg gcagtgtcca cagagggacc   420
tgccagcgac atatccttcc acccagcaat attgctgaca tacagtcgga agtgcattgc   480
atgtactcct cacaggcaga cgaagagccc agccagtgcc ctgactgtgt ggtgagtgct   540
ctaggaacca agtcctgat atcagaaaag gaccggttca tcaacttctt cgtaggcaat   600
accataaatt cctcggacca tccagatcat tcattgcatt cgatatcggt gagaaggcta   660
aaggaaacgc aagatgggtt caagtttttg acagaccagt cttacattga tgttctaccg   720
gagttcagag actcctaccc cattaaatat gtccacgcct tgaaagcaa ccactttat   780
tacttttga cagtccagcg agaaactcta gatgctcaga cttttcacac gagaataatc   840
aggttctgtt ctgtagactc tggattgcat tcctacatgg aaatgcctct ggagtgtatt   900
ctcacggaaa agagaagaaa gagatccaca agggaggaag tgtttaatat tctccaagct   960
gcatatgtca gtaagcctgg ggcccatctc gctaaacaaa taggtgccaa cctgaatgat  1020
gacattctct atggagtgtt cgcacaaagc aagccagatt ctgctgaacc aatgaatcgc  1080
tctgccgtct gtgcgttccc tatcaaatat gtcaatgaat tcttcaacaa gatcgtcaac  1140
aaaaacaatg tgagatgtct tcagcacttt tatggaccca accacgaaca ctgctttaat  1200
aggacacttt tgagaaattc atcgggctgt gaagcgcgca atgatgaata tcgaacggag  1260
ttcactacag ctttgcagcg cgttgactta ttcatgggcc agttcaacca gtcctctta  1320
acgtctatat ccaccttcat caaaggagac ctcaccattg ctaatcttgg acgtccgag  1380
ggtcgcttca tgcaggtcgt ggtttctcga tcaggattgt cgaccccctca cgtgaacttc  1440
cgcctggact cccaccccgt gtctccagaa gcaattgtgg agcacccact aaaccaaaac  1500
ggctacacac tcgttgtcac tgggaagaag atcaccagga tcccactgaa tggcttaggc  1560
tgtgagcatt ttcagtcctg cagtcagtgt ctctccgccc ctcccttgt gcagtgtggc  1620
tggtgccacg atagatgtgt gcacctggag gaatgtccca ctggagcgtg gactcaggag  1680
gtctgtctgc ctgcaatcta tgaggttttc ccaactagtg caccccctgga aggagggaca  1740
gtgctgactg tatgtggctg ggacttcgga ttcaggagga ataataaatt tgatttaaag  1800
aaaaccaaag ttttccttgg aaatgagagc tgcaccttga ccttaagtga gcacaacaa  1860
aatatgctga aatgcacagt tggccctgca gtgaacgagc atttcaatat atccataatt  1920
```

-continued

```
atttcaaatg gtcgagggac agcacaatat agtacatttt cgtatgtgga tcctattata    1980
acaagtattt ctccaagtta tggtcccaag aatggtggca ccttgctcac tttaactgga    2040
aaatacctca acagtgggaa ttctagacac atttcaatgg gtggaaaaac atgtacttta    2100
aaaagtgtgt cagatagtat tctcgaatgt tataccccag ctcaagccac tgcaactgag    2160
tttcctatta aattgaaaat tgacctagcc aaccgagaga tgaacagctt cagttaccag    2220
gaagacccca ttgtctatgc aattcatcca acgaaatctt ttattagtgg tgggagcaca    2280
ataacagctg ttggaaaaaa cctgaattca gtgagtgtcc tgaggatggt aatagatgtc    2340
catgaaacaa gaaggaactt tacagtggca tgtcaacatc gctctaattc agagataatc    2400
tgttgtacga ctccttcact gcaacagctg aatctgcaac tccctctgaa aaccaaagcc    2460
tttttcatgt tagatgggat ccattccaaa tactttgatc tcatttatgt acataatcct    2520
gtgtttaagc ttttgaaaa gccagtgatg atctcaatag gcaatgaaaa tgtactggaa    2580
attaagggaa atgatattga ccctgaagca gttaaaggcg aagtgttaaa agttggaaat    2640
aagagctgtg agactatcta ctcagattct aaagccgttt tatgcaaggt ccccaatgac    2700
ctgctgaaat tgaacaacga gctaaatata gagtggaagc aagcagtttc ttcaaccgtc    2760
cttggaaaag taatagttca accagatcag aatttcacag gattgattgc tggtgttatc    2820
tcaatatcaa caatagtctt attattactc ggacttttcc tgtggctgaa aaggaaaaag    2880
caaattaaag atctgagcag tgaattagtt cgctatgatg caagagtaca cactcctcat    2940
ttggataggc ttgtaagtgc ccgaagtgta agcccaacta cagaaatggt ttcaaatgaa    3000
tctgtagact accgagctac ttttccagaa gaccagtttc ctaattcatc tcagaatgga    3060
tcatgcagac aagtacaata tcctctgacg gacctgtccc ccatgcttac tagtggggac    3120
tctgatatat ccagtccatt attgcaaaat actgtccaca ttgacctcag tgctctaaat    3180
ccagagctgg tgcaggcagt ccagcatgta gtgattgggc ccagtagcct gattgtgcat    3240
ttcaatgaag tcataggaag aggacatttt gggtgtgtat accatgggac tttgttggac    3300
aatgacgaca aaaaaattca ctgtgctgtg aaatccctga atagaatcac tgacatagga    3360
gaagtttccc agtttctgac cgagggaatc atcatgaaag attttagtca tccaaacgta    3420
ctctcactct tgggaatctg ccttcgaagt gagggtctc cactggtggt cctaccatac    3480
atgaaacatg gagatcttcg aaatttcatt agaaatgaga ctcataaccc aactgtaaaa    3540
gatcttattg gctttggtct tcaagtagcc aaaggcatga aatatcttgc aagcaaaaag    3600
tttgtccaca gagacttggc tgcaagaaac tgtatgctgg atgaaaaatt cactgtcaag    3660
gttgctgatt ttggtcttgc cagagacatg tatgataaag aatactacag cgtacacaac    3720
aaaacaggcg ccaaactacc agtgaagtgg atggctttag aaagtctgca aactcagaag    3780
tttaccacca gtcagatgt gtggtccttt ggcgtgctcc tctgggaact gatgacaaga    3840
ggagcaccac cttatcctga cgtcaacacc tttgatataa cagtttactt gttgcaaggc    3900
agaaggctcc tgcaacccga atactgccca gatcccttat acgaagtgat gctaaaatgc    3960
tggcacccta gagctgaact gcgcccatct ttttctgaac tggtctccag gatatcagca    4020
atattctcta ctttcattgg ggagcactat gtccatgtga acgccactta tgtgaatgtc    4080
aaatgtgttg ctccataccc ttctctcttg tcatcacaag ataacattga tggcgagggg    4140
gacacatga                                                           4149
```

```
<210> SEQ ID NO 2
<211> LENGTH: 4149
```

<212> TYPE: DNA
<213> ORGANISM: Canis familiaris
<220> FEATURE:
<223> OTHER INFORMATION: canine Met (hepatocyte growth factor (HGF), scatter factor) G1630A mutant

<400> SEQUENCE: 2

| | | |
|---|---|---|
| atgaaggctc ctgctgtgct tgcacctggc atccttgtgc ttctgtttac cttggtgcag | 60 |
| aagagctatg gggagtgcaa agaggcacta gtaaagtctg agatgaatgt gaacatgaag | 120 |
| tatcagcttc ccaacttcac tgccgaaaca cccatccaga atgttgtttt acacaagcat | 180 |
| catatttacc ttggtgcagt taactatatt tacgttttaa atgacaaaga ccttcagaag | 240 |
| gttgctgagt acaagactgg gcccgtgctg aacacccag attgttcccc atgtcaggac | 300 |
| tgcagccaca aagccaattt atcaggtggt gtttgggaag ataacatcaa catggctctg | 360 |
| cttgttgaca catactacga tgaccaactc attagctgtg gcagtgtcca cagagggacc | 420 |
| tgccagcgac atatccttcc acccagcaat attgctgaca tacagtcgga agtgcattgc | 480 |
| atgtactcct cacaggcaga cgaagagccc agccagtgcc ctgactgtgt ggtgagtgct | 540 |
| ctaggaacca aagtcctgat atcagaaaag gaccggttca tcaacttctt cgtaggcaat | 600 |
| accataaatt cctcggacca tccagatcat tcattgcatt cgatatcggt gagaaggcta | 660 |
| aaggaaacgc aagatgggtt caagtttttg acagaccagt cttacattga tgttctaccg | 720 |
| gagttcagag actcctaccc cattaaatat gtccacgcct ttgaaagcaa ccactttatt | 780 |
| tacttttttga cagtccagcg agaaaactcta gatgctcaga cttttcacac agaataatc | 840 |
| aggttctgtt ctgtagactc tggattgcat tcctacatgg aaatgcctct ggagtgtatt | 900 |
| ctcacggaaa agaagaaaa gagatccaca agggaggaag tgtttaatat tctccaagct | 960 |
| gcatatgtca gtaagcctgg ggcccatctc gctaaacaaa taggtgccaa cctgaatgat | 1020 |
| gacattctct atgagtgtt cgcacaaagc aagccagatt ctgctgaacc aatgaatcgc | 1080 |
| tctgccgtct gtgcgttccc tatcaaatat gtcaatgaat cttcaacaa gatcgtcaac | 1140 |
| aaaaacaatg tgagatgtct tcagcacttt tatggaccca accacgaaca ctgctttaat | 1200 |
| aggacacttt tgagaaattc atcgggctgt gaagcgcgca tgatgaata tcgaacggag | 1260 |
| ttcactacag ctttgcagcg cgttgactta ttcatgggcc agttcaacca agtcctctta | 1320 |
| acgtctatat ccaccttcat caaaggagac ctcaccattg ctaatcttgg gacgtccgag | 1380 |
| ggtcgcttca tgcaggtcgt ggtttctcga tcaggattgt cgacccctca cgtgaacttc | 1440 |
| cgcctggact cccaccccgt gtctccagaa gcaattgtgg agcacccact aaaccaaaac | 1500 |
| ggctacacac tcgttgtcac tgggaagaag atcaccagga tcccactgaa tggcttaggc | 1560 |
| tgtgagcatt ttcagtcctg cagtcagtgt ctctccgccc ctccctttgt gcagtgtggc | 1620 |
| tggtgccaca atagatgtgt gcacctggag gaatgtccca ctggagcgtg gactcaggag | 1680 |
| gtctgtctgc ctgcaatcta tgaggttttc ccaactagtg caccctgga aggagggaca | 1740 |
| gtgctgactg tatgtggctg ggacttcgga ttcaggagga ataataaatt tgatttaaag | 1800 |
| aaaaccaaag ttttccttgg aaatgagagc tgcaccttga ccttaagtga gcacacaaca | 1860 |
| aatatgctga atgcacagt tggccctgca gtgaacgagc atttcaatat atccataatt | 1920 |
| atttcaaatg gtcgagggac agcacaatat agtgcatttt cgtatgtgga tcctattata | 1980 |
| acaagtattt ctccaagtta tggtccaag aatggtggca ccttgctcac tttaactgga | 2040 |
| aaatacctca cagtgggaa ttctagacac atttcaatgg gtggaaaaac atgtacttta | 2100 |
| aaaagtgtgt cagatagtat tctcgaatgt tatacccag ctcaagccac tgcaactgag | 2160 |

-continued

```
tttcctatta aattgaaaat tgacctagcc aaccgagaga tgaacagctt cagttaccag     2220
gaagacccca ttgtctatgc aattcatcca acgaaatctt ttattagtgg tgggagcaca     2280
ataacagctg ttggaaaaaa cctgaattca gtgagtgtcc tgaggatggt aatagatgtc     2340
catgaaacaa gaaggaactt tacagtggca tgtcaacatc gctctaattc agagataatc     2400
tgttgtacga ctccttcact gcaacagctg aatctgcaac tccctctgaa aaccaaagcc     2460
tttttcatgt tagatgggat ccattccaaa tactttgatc tcatttatgt acataatcct     2520
gtgtttaagc cttttgaaaa gccagtgatg atctcaatag gcaatgaaaa tgtactggaa     2580
attaagggaa atgatattga ccctgaagca gttaaaggcg aagtgttaaa agttggaaat     2640
aagagctgtg agactatcta ctcagattct aaagccgttt tatgcaaggt ccccaatgac     2700
ctgctgaaat tgaacaacga gctaaatata gagtggaagc aagcagtttc ttcaaccgtc     2760
cttggaaaag taatagttca accagatcag aatttcacag gattgattgc tggtgttatc     2820
tcaatatcaa caatagtctt attattactc ggacttttcc tgtggctgaa aaggaaaaag     2880
caaattaaag atctgggcag tgaattagtt cgctatgatg caagagtaca cactcctcat     2940
ttggataggc ttgtaagtgc ccgaagtgta agcccaacta cagaaatggt ttcaaatgaa     3000
tctgtagact accgagctac ttttccagaa gaccagtttc ctaattcatc tcagaatgga     3060
tcatgcagac aagtacaata tcctctgacg gacctgtccc ccatgcttac tagtgggac      3120 tctgatatat ccagtccatt attgcaaaat actgtccaca ttgacctcag tgctctaaat     3180
ccagagctgg tgcaggcagt ccagcatgta gtgattgggc ccagtagcct gattgtgcat     3240
ttcaatgaag tcataggaag aggacatttt gggtgtgtat accatgggac tttgttggac     3300
aatgacgaca aaaaaattca ctgtgctgtg aaatccctga atagaatcac tgacatagga     3360
gaagtttccc agtttctgac cgagggaatc atcatgaaag attttagtca tccaaacgta     3420
ctctcactct tgggaatctg ccttcgaagt gaggggtctc cactggtggt cctaccatac     3480
atgaaacatg gagatcttcg aaatttcatt agaaatgaga ctcataaccc aactgtaaaa     3540
gatcttattg gctttggtct tcaagtagcc aaaggcatga aatatcttgc aagcaaaaag     3600
tttgtccaca gagacttggc tgcaagaaac tgtatgctgg atgaaaaatt cactgtcaag     3660
gttgctgatt ttggtcttgc cagagacatg tatgataaag aatactacag cgtacacaac     3720
aaaacaggcg ccaaactacc agtgaagtgg atggctttag aaagtctgca aactcagaag     3780
tttaccacca gtcagatgt gtggtccttt ggcgtgctcc tctgggaact gatgacaaga     3840
ggagcaccac cttatcctga cgtcaacacc tttgatataa cagtttactt gttgcaaggc     3900
agaaggctcc tgcaacccga atactgccca gatcccttat acgaagtgat gctaaaatgc     3960
tggcacccta gagctgaact gcgcccatct ttttctgaac tggtctccag gatatcagca     4020
atattctcta ctttcattgg ggagcactat gtccatgtga acgccactta tgtgaatgtc     4080
aaatgtgttg ctccataccc ttctctcttg tcatcacaag ataacattga tggcgagggg     4140
gacacatga                                                             4149
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:forward
     (sense) 5' primer for amplification of canine Met
     (hepatocyte growth factor (HGF), scatter factor)
     G966S (G2896A) mutant

```
<400> SEQUENCE: 3
gcaatccacg agcccatgag                                              20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:reverse
      (antisense) 3' primer for amplification of canine
      Met (hepatocyte growth factor (HGF), scatter
      factor) G966S (G2896A) mutant

<400> SEQUENCE: 4
gtagttgggc ttacacttcg gg                                           22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:forward 5'
      primer for amplification of canine Met (hepatocyte
      growth factor (HGF), scatter factor) D544N mutant

<400> SEQUENCE: 5
gtcctgcagt cagtgtctct ccg                                          23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:reverse 3'
      primer for amplification of canine Met (hepatocyte
      growth factor (HGF), scatter factor) D544N mutant

<400> SEQUENCE: 6
ggtgcagctc tcatttccaa gg                                           22

<210> SEQ ID NO 7
<211> LENGTH: 1382
<212> TYPE: PRT
<213> ORGANISM: Canis familiaris
<220> FEATURE:
<223> OTHER INFORMATION: canine Met (hepatocyte growth factor (HGF),
      scatter factor) D544N mutant

<400> SEQUENCE: 7

Met Lys Ala Pro Ala Val Leu Ala Pro Gly Ile Leu Val Leu Leu Phe
 1               5                  10                  15

Thr Leu Val Gln Lys Ser Tyr Gly Glu Cys Lys Glu Ala Leu Val Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Val Leu His Lys His Ile Tyr Leu
        50                  55                  60

Gly Ala Val Asn Tyr Ile Tyr Val Leu Asn Asp Lys Asp Leu Gln Lys
65                  70                  75                  80

Val Ala Glu Tyr Lys Thr Gly Pro Val Leu Glu His Pro Asp Cys Ser
                85                  90                  95

Pro Cys Gln Asp Cys Ser His Lys Ala Asn Leu Ser Gly Gly Val Trp
            100                 105                 110
```

-continued

```
Glu Asp Asn Ile Asn Met Ala Leu Leu Val Asp Thr Tyr Tyr Asp Asp
            115                 120                 125

Gln Leu Ile Ser Cys Gly Ser Val His Arg Gly Thr Cys Gln Arg His
            130                 135                 140

Ile Leu Pro Pro Ser Asn Ile Ala Asp Ile Gln Ser Glu Val His Cys
145                 150                 155                 160

Met Tyr Ser Ser Gln Ala Asp Glu Glu Pro Ser Gln Cys Pro Asp Cys
            165                 170                 175

Val Val Ser Ala Leu Gly Thr Lys Val Leu Ile Ser Glu Lys Asp Arg
            180                 185                 190

Phe Ile Asn Phe Phe Val Gly Asn Thr Ile Asn Ser Ser Asp His Pro
            195                 200                 205

Asp His Ser Leu His Ser Ile Ser Val Arg Arg Leu Lys Glu Thr Gln
            210                 215                 220

Asp Gly Phe Lys Phe Leu Thr Asp Gln Ser Tyr Ile Asp Val Leu Pro
225                 230                 235                 240

Glu Phe Arg Asp Ser Tyr Pro Ile Lys Tyr Val His Ala Phe Glu Ser
            245                 250                 255

Asn His Phe Ile Tyr Phe Leu Thr Val Gln Arg Glu Thr Leu Asp Ala
            260                 265                 270

Gln Thr Phe His Thr Arg Ile Ile Arg Phe Cys Ser Val Asp Ser Gly
            275                 280                 285

Leu His Ser Tyr Met Glu Met Pro Leu Glu Cys Ile Leu Thr Glu Lys
            290                 295                 300

Arg Arg Lys Arg Ser Thr Arg Glu Glu Val Phe Asn Ile Leu Gln Ala
305                 310                 315                 320

Ala Tyr Val Ser Lys Pro Gly Ala His Leu Ala Lys Gln Ile Gly Ala
            325                 330                 335

Asn Leu Asn Asp Asp Ile Leu Tyr Gly Val Phe Ala Gln Ser Lys Pro
            340                 345                 350

Asp Ser Ala Glu Pro Met Asn Arg Ser Ala Val Cys Ala Phe Pro Ile
            355                 360                 365

Lys Tyr Val Asn Glu Phe Phe Asn Lys Ile Val Asn Lys Asn Asn Val
370                 375                 380

Arg Cys Leu Gln His Phe Tyr Gly Pro Asn His Glu His Cys Phe Asn
385                 390                 395                 400

Arg Thr Leu Leu Arg Asn Ser Ser Gly Cys Glu Ala Arg Asn Asp Glu
            405                 410                 415

Tyr Arg Thr Glu Phe Thr Thr Ala Leu Gln Arg Val Asp Leu Phe Met
            420                 425                 430

Gly Gln Phe Asn Gln Val Leu Leu Thr Ser Ile Ser Thr Phe Ile Lys
            435                 440                 445

Gly Asp Leu Thr Ile Ala Asn Leu Gly Thr Ser Glu Gly Arg Phe Met
            450                 455                 460

Gln Val Val Val Ser Arg Ser Gly Leu Ser Thr Pro His Val Asn Phe
465                 470                 475                 480

Arg Leu Asp Ser His Pro Val Ser Pro Glu Ala Ile Val Glu His Pro
            485                 490                 495

Leu Asn Gln Asn Gly Tyr Thr Leu Val Val Thr Gly Lys Lys Ile Thr
            500                 505                 510

Arg Ile Pro Leu Asn Gly Leu Gly Cys Glu His Phe Gln Ser Cys Ser
            515                 520                 525
```

-continued

```
Gln Cys Leu Ser Ala Pro Pro Phe Val Gln Cys Gly Trp Cys His Asn
    530                 535                 540
Arg Cys Val His Leu Glu Glu Cys Pro Thr Gly Ala Trp Thr Gln Glu
545                 550                 555                 560
Val Cys Leu Pro Ala Ile Tyr Glu Val Phe Pro Thr Ser Ala Pro Leu
                565                 570                 575
Glu Gly Gly Thr Val Leu Thr Val Cys Gly Trp Asp Phe Gly Phe Arg
            580                 585                 590
Arg Asn Asn Lys Phe Asp Leu Lys Lys Thr Lys Val Phe Leu Gly Asn
        595                 600                 605
Glu Ser Cys Thr Leu Thr Leu Ser Glu Ser Thr Thr Asn Met Leu Lys
    610                 615                 620
Cys Thr Val Gly Pro Ala Val Asn Glu His Phe Asn Ile Ser Ile Ile
625                 630                 635                 640
Ile Ser Asn Gly Arg Gly Thr Ala Gln Tyr Ser Thr Phe Ser Tyr Val
                645                 650                 655
Asp Pro Ile Ile Thr Ser Ile Ser Pro Ser Tyr Gly Pro Lys Asn Gly
            660                 665                 670
Gly Thr Leu Leu Thr Leu Thr Gly Lys Tyr Leu Asn Ser Gly Asn Ser
        675                 680                 685
Arg His Ile Ser Met Gly Gly Lys Thr Cys Thr Leu Lys Ser Val Ser
    690                 695                 700
Asp Ser Ile Leu Glu Cys Tyr Thr Pro Ala Gln Ala Thr Ala Thr Glu
705                 710                 715                 720
Phe Pro Ile Lys Leu Lys Ile Asp Leu Ala Asn Arg Glu Met Asn Ser
                725                 730                 735
Phe Ser Tyr Gln Glu Asp Pro Ile Val Tyr Ala Ile His Pro Thr Lys
            740                 745                 750
Ser Phe Ile Ser Gly Gly Ser Thr Ile Thr Ala Val Gly Lys Asn Leu
        755                 760                 765
Asn Ser Val Ser Val Leu Arg Met Val Ile Asp Val His Glu Thr Arg
    770                 775                 780
Arg Asn Phe Thr Val Ala Cys Gln His Arg Ser Asn Ser Glu Ile Ile
785                 790                 795                 800
Cys Cys Thr Thr Pro Ser Leu Gln Gln Leu Asn Leu Gln Leu Pro Leu
                805                 810                 815
Lys Thr Lys Ala Phe Phe Met Leu Asp Gly Ile His Ser Lys Tyr Phe
            820                 825                 830
Asp Leu Ile Tyr Val His Asn Pro Val Phe Lys Pro Phe Glu Lys Pro
        835                 840                 845
Val Met Ile Ser Ile Gly Asn Glu Asn Val Leu Glu Ile Lys Gly Asn
    850                 855                 860
Asp Ile Asp Pro Glu Ala Val Lys Gly Glu Val Leu Lys Val Gly Asn
865                 870                 875                 880
Lys Ser Cys Glu Thr Ile Tyr Ser Asp Ser Lys Ala Val Leu Cys Lys
                885                 890                 895
Val Pro Asn Asp Leu Leu Lys Leu Asn Glu Leu Asn Ile Glu Trp
            900                 905                 910
Lys Gln Ala Val Ser Ser Thr Val Leu Gly Lys Val Ile Val Gln Pro
        915                 920                 925
Asp Gln Asn Phe Thr Gly Leu Ile Ala Gly Val Ile Ser Ile Ser Thr
    930                 935                 940
Ile Val Leu Leu Leu Leu Gly Leu Phe Leu Trp Leu Lys Arg Lys Lys
```

-continued

```
            945                 950                 955                 960
Gln Ile Lys Asp Leu Gly Ser Glu Leu Val Arg Tyr Asp Ala Arg Val
                965                 970                 975
His Thr Pro His Leu Asp Arg Leu Val Ser Ala Arg Ser Val Ser Pro
            980                 985                 990
Thr Thr Glu Met Val Ser Asn Glu Ser Val Asp Tyr Arg Ala Thr Phe
            995                 1000                1005
Pro Glu Asp Gln Phe Pro Asn Ser Ser Gln Asn Gly Ser Cys Arg Gln
    1010                1015                1020
Val Gln Tyr Pro Leu Thr Asp Leu Ser Pro Met Leu Thr Ser Gly Asp
1025                1030                1035                1040
Ser Asp Ile Ser Ser Pro Leu Leu Gln Asn Thr Val His Ile Asp Leu
                1045                1050                1055
Ser Ala Leu Asn Pro Glu Leu Val Gln Ala Val Gln His Val Val Ile
            1060                1065                1070
Gly Pro Ser Ser Leu Ile Val His Phe Asn Glu Val Ile Gly Arg Gly
        1075                1080                1085
His Phe Gly Cys Val Tyr His Gly Thr Leu Leu Asp Asn Asp Asp Lys
    1090                1095                1100
Lys Ile His Cys Ala Val Lys Ser Leu Asn Arg Ile Thr Asp Ile Gly
1105                1110                1115                1120
Glu Val Ser Gln Phe Leu Thr Glu Gly Ile Ile Met Lys Asp Phe Ser
                1125                1130                1135
His Pro Asn Val Leu Ser Leu Leu Gly Ile Cys Leu Arg Ser Glu Gly
            1140                1145                1150
Ser Pro Leu Val Val Leu Pro Tyr Met Lys His Gly Asp Leu Arg Asn
        1155                1160                1165
Phe Ile Arg Asn Glu Thr His Asn Pro Thr Val Lys Asp Leu Ile Gly
    1170                1175                1180
Phe Gly Leu Gln Val Ala Lys Gly Met Lys Tyr Leu Ala Ser Lys Lys
1185                1190                1195                1200
Phe Val His Arg Asp Leu Ala Ala Arg Asn Cys Met Leu Asp Glu Lys
                1205                1210                1215
Phe Thr Val Lys Val Ala Asp Phe Gly Leu Ala Arg Asp Met Tyr Asp
            1220                1225                1230
Lys Glu Tyr Tyr Ser Val His Asn Lys Thr Gly Ala Lys Leu Pro Val
        1235                1240                1245
Lys Trp Met Ala Leu Glu Ser Leu Gln Thr Gln Lys Phe Thr Thr Lys
    1250                1255                1260
Ser Asp Val Trp Ser Phe Gly Val Leu Leu Trp Glu Leu Met Thr Arg
1265                1270                1275                1280
Gly Ala Pro Pro Tyr Pro Asp Val Asn Thr Phe Asp Ile Thr Val Tyr
                1285                1290                1295
Leu Leu Gln Gly Arg Arg Leu Leu Gln Pro Glu Tyr Cys Pro Asp Pro
            1300                1305                1310
Leu Tyr Glu Val Met Leu Lys Cys Trp His Pro Arg Ala Glu Leu Arg
        1315                1320                1325
Pro Ser Phe Ser Glu Leu Val Ser Arg Ile Ser Ala Ile Phe Ser Thr
    1330                1335                1340
Phe Ile Gly Glu His Tyr Val His Val Asn Ala Thr Tyr Val Asn Val
1345                1350                1355                1360
Lys Cys Val Ala Pro Tyr Pro Ser Leu Leu Ser Ser Gln Asp Asn Ile
                1365                1370                1375
```

```
Asp Gly Glu Gly Asp Thr
        1380

<210> SEQ ID NO 8
<211> LENGTH: 4149
<212> TYPE: DNA
<213> ORGANISM: Canis familiaris
<220> FEATURE:
<223> OTHER INFORMATION: canine Met (hepatocyte growth factor (HGF),
      scatter factor) wild-type

<400> SEQUENCE: 8
atgaaggctc ctgctgtgct tgcacctggc atccttgtgc ttctgtttac cttggtgcag      60
aagagctatg gggagtgcaa agaggcacta gtaaagtctg agatgaatgt gaacatgaag     120
tatcagcttc ccaacttcac tgccgaaaca cccatccaga atgttgtttt acacaagcat     180
catatttacc ttggtgcagt taactatatt tacgttttaa atgacaaaga ccttcagaag     240
gttgctgagt acaagactgg gcccgtgctg aacacccag attgttcccc atgtcaggac      300
tgcagccaca agccaatttt atcaggtggt gtttgggaag ataacatcaa catggctctg     360
cttgttgaca catactacga tgaccaactc attagctgtg gcagtgtcca cagagggacc     420
tgccagcgac atatccttcc acccagcaat attgctgaca tacagtcgga agtgcattgc     480
atgtactcct cacaggcaga cgaagagccc agccagtgcc ctgactgtgt ggtgagtgct     540
ctaggaacca aagtcctgat atcagaaaag gaccggttca tcaacttctt cgtaggcaat     600
accataaatt cctcggacca tccagatcat tcattgcatt cgatatcggt gagaaggcta     660
aaggaaacgc aagatgggtt caagtttttg acagaccagt cttacattga tgttctaccg     720
gagttcagag actcctaccc cattaaatat gtccacgcct tgaaagcaa ccactttat      780 tactttttga cagtccagcg agaaactcta gatgctcaga cttttcacac gagaataatc     840
aggttctgtt ctgtagactc tggattgcat tcctacatgg aaatgcctct ggagtgtatt     900
ctcacggaaa agagaagaa gagatccaca agggaggaag tgtttaatat tctccaagct     960
gcatatgtca gtaagcctgg ggcccatctc gctaaacaaa taggtgccaa cctgaatgat    1020
gacattctct atggagtgtt cgcacaaagc aagccagatt ctgctgaacc aatgaatcgc    1080
tctgccgtct gtgcgttccc tatcaaatat gtcaatgaat tcttcaacaa gatcgtcaac    1140
aaaaacaatg tgagatgtct tcagcacttt tatggaccca accacgaaca ctgctttaat    1200
aggacacttt tgagaaattc atcgggctgt gaagcgcgca atgatgaata tcgaacggag    1260
ttcactacag ctttgcagcg cgttgactta ttcatgggcc agttcaacca agtcctctta    1320
acgtctatat ccacccttcat caaaggagac ctcaccattg ctaatcttgg acgtccgag    1380 ggtcgcttca tgcaggtcgt ggtttctcga tcaggattgt cgacccctca cgtgaacttc    1440
cgcctggact cccaccccgt gtctccagaa gcaattgtgg agcacccact aaaccaaaac    1500
ggctacacac tcgttgtcac tgggaagaag atcaccagga tcccactgaa tggcttaggc    1560
tgtgagcatt ttcagtcctg cagtcagtgt ctctccgccc ctccctttgt gcagtgtggc    1620
tggtgccacg atagatgtgt gcacctggag gaatgtccca ctggagcgtg gactcaggag    1680
gtctgtctgc ctgcaatcta tgaggttttc ccaactagtg caccctggaa ggagggaca     1740 gtgctgactg tatgtggctg ggacttcgga ttcaggagga taataaaatt tgatttaaag    1800
aaaaccaaag ttttccttgg aaatgagagc tgcaccttga ccttaagtga gcacaacaa     1860 aatatgctga aatgcacagt tggccctgca gtgaacgagc atttcaatat atccataatt    1920
```

```
atttcaaatg gtcgagggac agcacaatat agtacatttt cgtatgtgga tcctattata    1980
acaagtattt ctccaagtta tggtcccaag aatggtggca ccttgctcac tttaactgga    2040
aaatacctca acagtgggaa ttctagacac atttcaatgg gtggaaaaac atgtacttta    2100
aaaagtgtgt cagatagtat tctcgaatgt tatacccag ctcaagccac tgcaactgag     2160
tttcctatta aattgaaaat tgacctagcc aaccgagaga tgaacagctt cagttaccag    2220
gaagacccca ttgtctatgc aattcatcca acgaaatctt ttattagtgg tgggagcaca    2280
ataacagctg ttgaaaaaaa cctgaattca gtgagtgtcc tgaggatggt aatagatgtc    2340
catgaaacaa gaaggaactt tacagtggca tgtcaacatc gctctaattc agagataatc    2400
tgttgtacga ctccttcact gcaacagctg aatctgcaac tccctctgaa accaaagcc    2460
tttttcatgt tagatgggat ccattccaaa tactttgatc tcatttatgt acataatcct    2520
gtgtttaagc cttttgaaaa gccagtgatg atctcaatag gcaatgaaaa tgtactggaa    2580
attaagggaa atgatattga ccctgaagca gttaaaggcg aagtgttaaa agttggaaat    2640
aagagctgtg agactatcta ctcagattct aaagccgttt tatgcaaggt ccccaatgac    2700
ctgctgaaat tgaacaacga gctaaatata gagtggaagc aagcagtttc ttcaaccgtc    2760
cttggaaaag taatagttca accagatcag aatttcacag gattgattgc tggtgttatc    2820
tcaatatcaa caatagtctt attattactc ggacttttcc tgtggctgaa aaggaaaaag    2880
caaattaaag atctgggcag tgaattagtt cgctatgatg caagagtaca cactcctcat    2940
ttggataggc ttgtaagtgc ccgaagtgta agcccaacta cagaaatggt ttcaaatgaa    3000
tctgtagact accgagctac ttttccagaa gaccagtttc ctaattcatc tcagaatgga    3060
tcatgcagac aagtacaata tcctctgacg gacctgtccc ccatgcttac tagtggggac    3120
tctgatatat ccagtccatt attgcaaaat actgtccaca ttgacctcag tgctctaaat    3180
ccagagctgg tgcaggcagt ccagcatgta gtgattgggc ccagtagcct gattgtgcat    3240
ttcaatgaag tcataggaag aggacatttt gggtgtgtat accatgggac tttgttggac    3300
aatgacgaca aaaaaattca ctgtgctgtg aaatccctga atagaatcac tgacatagga    3360
gaagtttccc agtttctgac cgagggaatc atcatgaaag attttagtca tccaaacgta    3420
ctctcactct tgggaatctg ccttcgaagt gagggtctc cactggtggt cctaccatac    3480
atgaaacatg gagatcttcg aaatttcatt agaaatgaga ctcataaccc aactgtaaaa    3540
gatcttattg gctttggtct tcaagtagcc aaaggcatga atatcttgc aagcaaaaag    3600
tttgtccaca gagacttggc tgcaagaaac tgtatgctgg atgaaaaatt cactgtcaag    3660
gttgctgatt ttggtcttgc cagagacatg tatgataaag aatactacag cgtacacaac    3720
aaaacaggcg ccaaactacc agtgaagtgg atggctttag aaagtctgca aactcagaag    3780
tttaccacca gtcagatgt gtggtccttt ggcgtgctcc tctgggaact gatgacaaga    3840
ggagcaccac cttatcctga cgtcaacacc tttgatataa cagtttactt gttgcaaggc    3900
agaaggctcc tgcaacccga atactgccca gatcccttat acgaagtgat gctaaaatgc    3960
tggcacccta gagctgaact gcgcccatct ttttctgaac tggtctccag gatatcagca    4020
atattctcta ctttcattgg ggagcactat gtccatgtga acgccactta tgtgaatgtc    4080
aaatgtgttg ctccataccc ttctctcttg tcatcacaag ataacattga tggcgagggg    4140
gacacatga                                                            4149
```

<210> SEQ ID NO 9
<211> LENGTH: 1382

```
<212> TYPE: PRT
<213> ORGANISM: Canis familiaris
<220> FEATURE:
<223> OTHER INFORMATION: canine Met (hepatocyte growth factor (HGF),
      scatter factor) wild-type

<400> SEQUENCE: 9
```

| | | | | | | | | | | | | | | |
|---|---|---|---|---|---|---|---|---|---|---|---|---|---|---|
| Met | Lys | Ala | Pro | Ala | Val | Leu | Ala | Pro | Gly | Ile | Leu | Val | Leu | Leu | Phe |
| 1 | | | | 5 | | | | | 10 | | | | | 15 | |
| Thr | Leu | Val | Gln | Lys | Ser | Tyr | Gly | Glu | Cys | Lys | Glu | Ala | Leu | Val | Lys |
| | | | | 20 | | | | | 25 | | | | | 30 | |
| Ser | Glu | Met | Asn | Val | Asn | Met | Lys | Tyr | Gln | Leu | Pro | Asn | Phe | Thr | Ala |
| | | 35 | | | | | 40 | | | | | 45 | | | |
| Glu | Thr | Pro | Ile | Gln | Asn | Val | Val | Leu | His | Lys | His | Ile | Tyr | Leu | |
| | 50 | | | | | 55 | | | | | 60 | | | | |
| Gly | Ala | Val | Asn | Tyr | Ile | Tyr | Val | Leu | Asn | Asp | Lys | Asp | Leu | Gln | Lys |
| 65 | | | | | 70 | | | | | 75 | | | | | 80 |
| Val | Ala | Glu | Tyr | Lys | Thr | Gly | Pro | Val | Leu | Glu | His | Pro | Asp | Cys | Ser |
| | | | | 85 | | | | | 90 | | | | | 95 | |
| Pro | Cys | Gln | Asp | Cys | Ser | His | Lys | Ala | Asn | Leu | Ser | Gly | Gly | Val | Trp |
| | | | | 100 | | | | | 105 | | | | | 110 | |
| Glu | Asp | Asn | Ile | Asn | Met | Ala | Leu | Leu | Val | Asp | Thr | Tyr | Tyr | Asp | Asp |
| | | | 115 | | | | | 120 | | | | | 125 | | |
| Gln | Leu | Ile | Ser | Cys | Gly | Ser | Val | His | Arg | Gly | Thr | Cys | Gln | Arg | His |
| | 130 | | | | | 135 | | | | | 140 | | | | |
| Ile | Leu | Pro | Pro | Ser | Asn | Ile | Ala | Asp | Ile | Gln | Ser | Glu | Val | His | Cys |
| 145 | | | | | 150 | | | | | 155 | | | | | 160 |
| Met | Tyr | Ser | Ser | Gln | Ala | Asp | Glu | Pro | Ser | Gln | Cys | Pro | Asp | Cys | |
| | | | | 165 | | | | | 170 | | | | | 175 | |
| Val | Val | Ser | Ala | Leu | Gly | Thr | Lys | Val | Leu | Ile | Ser | Glu | Lys | Asp | Arg |
| | | | 180 | | | | | 185 | | | | | 190 | | |
| Phe | Ile | Asn | Phe | Phe | Val | Gly | Asn | Thr | Ile | Asn | Ser | Ser | Asp | His | Pro |
| | 195 | | | | | 200 | | | | | 205 | | | | |
| Asp | His | Ser | Leu | His | Ser | Ile | Ser | Val | Arg | Arg | Leu | Lys | Glu | Thr | Gln |
| | 210 | | | | | 215 | | | | | 220 | | | | |
| Asp | Gly | Phe | Lys | Phe | Leu | Thr | Asp | Gln | Ser | Tyr | Ile | Asp | Val | Leu | Pro |
| 225 | | | | | 230 | | | | | 235 | | | | | 240 |
| Glu | Phe | Arg | Asp | Ser | Tyr | Pro | Ile | Lys | Tyr | Val | His | Ala | Phe | Glu | Ser |
| | | | | 245 | | | | | 250 | | | | | 255 | |
| Asn | His | Phe | Ile | Tyr | Phe | Leu | Thr | Val | Gln | Arg | Glu | Thr | Leu | Asp | Ala |
| | | | 260 | | | | | 265 | | | | | 270 | | |
| Gln | Thr | Phe | His | Thr | Arg | Ile | Ile | Arg | Phe | Cys | Ser | Val | Asp | Ser | Gly |
| | | 275 | | | | | 280 | | | | | 285 | | | |
| Leu | His | Ser | Tyr | Met | Glu | Met | Pro | Leu | Glu | Cys | Ile | Leu | Thr | Glu | Lys |
| | 290 | | | | | 295 | | | | | 300 | | | | |
| Arg | Arg | Lys | Arg | Ser | Thr | Arg | Glu | Glu | Val | Phe | Asn | Ile | Leu | Gln | Ala |
| 305 | | | | | 310 | | | | | 315 | | | | | 320 |
| Ala | Tyr | Val | Ser | Lys | Pro | Gly | Ala | His | Leu | Ala | Lys | Gln | Ile | Gly | Ala |
| | | | | 325 | | | | | 330 | | | | | 335 | |
| Asn | Leu | Asn | Asp | Asp | Ile | Leu | Tyr | Gly | Val | Phe | Ala | Gln | Ser | Lys | Pro |
| | | | 340 | | | | | 345 | | | | | 350 | | |
| Asp | Ser | Ala | Glu | Pro | Met | Asn | Arg | Ser | Ala | Val | Cys | Ala | Phe | Pro | Ile |
| | | 355 | | | | | 360 | | | | | 365 | | | |
| Lys | Tyr | Val | Asn | Glu | Phe | Phe | Asn | Lys | Ile | Val | Asn | Lys | Asn | Asn | Val |
| | | 370 | | | | | 375 | | | | | 380 | | | |

-continued

```
Arg Cys Leu Gln His Phe Tyr Gly Pro Asn His Glu His Cys Phe Asn
385                 390                 395                 400

Arg Thr Leu Leu Arg Asn Ser Ser Gly Cys Glu Ala Arg Asn Asp Glu
            405                 410                 415

Tyr Arg Thr Glu Phe Thr Thr Ala Leu Gln Arg Val Asp Leu Phe Met
                420                 425                 430

Gly Gln Phe Asn Gln Val Leu Leu Thr Ser Ile Ser Thr Phe Ile Lys
            435                 440                 445

Gly Asp Leu Thr Ile Ala Asn Leu Gly Thr Ser Glu Gly Arg Phe Met
450                 455                 460

Gln Val Val Ser Arg Ser Gly Leu Ser Thr Pro His Val Asn Phe
465                 470                 475                 480

Arg Leu Asp Ser His Pro Val Ser Pro Glu Ala Ile Val Glu His Pro
                485                 490                 495

Leu Asn Gln Asn Gly Tyr Thr Leu Val Val Thr Gly Lys Lys Ile Thr
            500                 505                 510

Arg Ile Pro Leu Asn Gly Leu Gly Cys Glu His Phe Gln Ser Cys Ser
            515                 520                 525

Gln Cys Leu Ser Ala Pro Pro Phe Val Gln Cys Gly Trp Cys His Asp
530                 535                 540

Arg Cys Val His Leu Glu Glu Cys Pro Thr Gly Ala Trp Thr Gln Glu
545                 550                 555                 560

Val Cys Leu Pro Ala Ile Tyr Glu Val Phe Pro Thr Ser Ala Pro Leu
                565                 570                 575

Glu Gly Gly Thr Val Leu Thr Val Cys Gly Trp Asp Phe Gly Phe Arg
            580                 585                 590

Arg Asn Asn Lys Phe Asp Leu Lys Lys Thr Lys Val Phe Leu Gly Asn
            595                 600                 605

Glu Ser Cys Thr Leu Thr Leu Ser Glu Ser Thr Thr Asn Met Leu Lys
            610                 615                 620

Cys Thr Val Gly Pro Ala Val Asn Glu His Phe Asn Ile Ser Ile Ile
625                 630                 635                 640

Ile Ser Asn Gly Arg Gly Thr Ala Gln Tyr Ser Thr Phe Ser Tyr Val
                645                 650                 655

Asp Pro Ile Ile Thr Ser Ile Ser Pro Ser Tyr Gly Pro Lys Asn Gly
                660                 665                 670

Gly Thr Leu Leu Thr Leu Thr Gly Lys Tyr Leu Asn Ser Gly Asn Ser
            675                 680                 685

Arg His Ile Ser Met Gly Gly Lys Thr Cys Thr Leu Lys Ser Val Ser
690                 695                 700

Asp Ser Ile Leu Glu Cys Tyr Thr Pro Ala Gln Ala Thr Ala Thr Glu
705                 710                 715                 720

Phe Pro Ile Lys Leu Lys Ile Asp Leu Ala Asn Arg Glu Met Asn Ser
                725                 730                 735

Phe Ser Tyr Gln Glu Asp Pro Ile Val Tyr Ala Ile His Pro Thr Lys
            740                 745                 750

Ser Phe Ile Ser Gly Gly Ser Thr Ile Thr Ala Val Gly Lys Asn Leu
            755                 760                 765

Asn Ser Val Ser Val Leu Arg Met Val Ile Asp His Glu Thr Arg
770                 775                 780

Arg Asn Phe Thr Val Ala Cys Gln His Arg Ser Asn Ser Glu Ile Ile
785                 790                 795                 800
```

-continued

Cys Cys Thr Thr Pro Ser Leu Gln Gln Leu Asn Leu Gln Leu Pro Leu
                805                 810                 815

Lys Thr Lys Ala Phe Phe Met Leu Asp Gly Ile His Ser Lys Tyr Phe
                820                 825                 830

Asp Leu Ile Tyr Val His Asn Pro Val Phe Lys Pro Phe Glu Lys Pro
                835                 840                 845

Val Met Ile Ser Ile Gly Asn Glu Asn Val Leu Glu Ile Lys Gly Asn
850                 855                 860

Asp Ile Asp Pro Glu Ala Val Lys Gly Glu Val Leu Lys Val Gly Asn
865                 870                 875                 880

Lys Ser Cys Glu Thr Ile Tyr Ser Asp Ser Lys Ala Val Leu Cys Lys
                885                 890                 895

Val Pro Asn Asp Leu Leu Lys Leu Asn Asn Glu Leu Asn Ile Glu Trp
                900                 905                 910

Lys Gln Ala Val Ser Ser Thr Val Leu Gly Lys Val Ile Val Gln Pro
                915                 920                 925

Asp Gln Asn Phe Thr Gly Leu Ile Ala Gly Val Ile Ser Ile Ser Thr
                930                 935                 940

Ile Val Leu Leu Leu Gly Leu Phe Leu Trp Leu Lys Arg Lys Lys
945                 950                 955                 960

Gln Ile Lys Asp Leu Gly Ser Glu Leu Val Arg Tyr Asp Ala Arg Val
                965                 970                 975

His Thr Pro His Leu Asp Arg Leu Val Ser Ala Arg Ser Val Ser Pro
                980                 985                 990

Thr Thr Glu Met Val Ser Asn Glu Ser Val Asp Tyr Arg Ala Thr Phe
                995                 1000                1005

Pro Glu Asp Gln Phe Pro Asn Ser Ser Gln Asn Gly Ser Cys Arg Gln
    1010                1015                1020

Val Gln Tyr Pro Leu Thr Asp Leu Ser Pro Met Leu Thr Ser Gly Asp
1025                1030                1035                1040

Ser Asp Ile Ser Ser Pro Leu Leu Gln Asn Thr Val His Ile Asp Leu
                1045                1050                1055

Ser Ala Leu Asn Pro Glu Leu Val Gln Ala Val Gln His Val Val Ile
                1060                1065                1070

Gly Pro Ser Ser Leu Ile Val His Phe Asn Glu Val Ile Gly Arg Gly
                1075                1080                1085

His Phe Gly Cys Val Tyr His Gly Thr Leu Leu Asp Asn Asp Asp Lys
    1090                1095                1100

Lys Ile His Cys Ala Val Lys Ser Leu Asn Arg Ile Thr Asp Ile Gly
1105                1110                1115                1120

Glu Val Ser Gln Phe Leu Thr Glu Gly Ile Ile Met Lys Asp Phe Ser
                1125                1130                1135

His Pro Asn Val Leu Ser Leu Leu Gly Ile Cys Leu Arg Ser Glu Gly
                1140                1145                1150

Ser Pro Leu Val Val Leu Pro Tyr Met Lys His Gly Asp Leu Arg Asn
                1155                1160                1165

Phe Ile Arg Asn Glu Thr His Asn Pro Thr Val Lys Asp Leu Ile Gly
    1170                1175                1180

Phe Gly Leu Gln Val Ala Lys Gly Met Lys Tyr Leu Ala Ser Lys Lys
1185                1190                1195                1200

Phe Val His Arg Asp Leu Ala Ala Arg Asn Cys Met Leu Asp Glu Lys
                1205                1210                1215

Phe Thr Val Lys Val Ala Asp Phe Gly Leu Ala Arg Asp Met Tyr Asp

```
                1220            1225            1230
Lys Glu Tyr Tyr Ser Val His Asn Lys Thr Gly Ala Lys Leu Pro Val
        1235            1240            1245

Lys Trp Met Ala Leu Glu Ser Leu Gln Thr Gln Lys Phe Thr Thr Lys
    1250            1255            1260

Ser Asp Val Trp Ser Phe Gly Val Leu Leu Trp Glu Leu Met Thr Arg
1265            1270            1275            1280

Gly Ala Pro Pro Tyr Pro Asp Val Asn Thr Phe Asp Ile Thr Val Tyr
            1285            1290            1295

Leu Leu Gln Gly Arg Arg Leu Leu Gln Pro Glu Tyr Cys Pro Asp Pro
        1300            1305            1310

Leu Tyr Glu Val Met Leu Lys Cys Trp His Pro Arg Ala Glu Leu Arg
        1315            1320            1325

Pro Ser Phe Ser Glu Leu Val Ser Arg Ile Ser Ala Ile Phe Ser Thr
    1330            1335            1340

Phe Ile Gly Glu His Tyr Val His Val Asn Ala Thr Tyr Val Asn Val
1345            1350            1355            1360

Lys Cys Val Ala Pro Tyr Pro Ser Leu Leu Ser Ser Gln Asp Asn Ile
            1365            1370            1375

Asp Gly Glu Gly Asp Thr
        1380
```

```
<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:forward
      primer for D544N mutation in cMet exon 4

<400> SEQUENCE: 10
caccaggatc ccactgaa                                              18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:reverse
      primer for D544N mutation in cMet exon 4

<400> SEQUENCE: 11
ttgcaggcag acagacct                                              18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:probe for
      D544N mutation in cMet exon 4

<400> SEQUENCE: 12
ccaggtgcac acatctat                                              18

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:M13 specific
      leader sequence to be added to 5' end of forward
``` primer for D544N mutation in cMet exon 4

<400> SEQUENCE: 13
agcgcataac aatttcacac agg                                                    23

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence:carboxy
      terminus of canine Met synthetic peptide for
      conjugation to carrier protein for mutant Met
      immunogen

<400> SEQUENCE: 14

Pro Tyr Pro Ser Leu Leu Ser Ser Gln Asp Asn Ile Asp Gly Glu Gly
 1               5                  10                  15

Asp Thr

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence:forward
      primer for generating wild-type canine Met

<400> SEQUENCE: 15
atgaaggctc ctgctgtgct tgcacctggc atccttg                                     37

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence:reverse
      primer for generating wild-type canine Met

<400> SEQUENCE: 16
gggaccaatc atgtgtcccc ctcgccatca atgttatctt gtg                              43

MUTANT MET AND USES THEREFOR

CROSS-REFERENCE TO RELATED APPLICATIONS

This application claims the benefit of U.S. Provisional Patent Application No. 60/602,778, filed Aug. 18, 2004, the disclosure of which is hereby incorporated by reference in its entirety for all purposes.

BACKGROUND OF THE INVENTION

Cancer is increasingly common in canines. Canine cancers include solid tumors and lymphomas such as, e.g., cancers of the mammary glands, prostate, oropharynx, skin, gastrointestinal tract, lungs and bone. A number of canine cancers are highly aggressive.

Recently, studies have been directed toward elucidating the biological mechanism underlying canine cancers. Dysregulation of growth factor receptors (also known as receptor tyrosine kinases, RTKs) is a common mechanism by which normal cells can undergo malignant transformation. One particular RTK termed Met is over-expressed in 60-100% of human OSA, and is known to be aberrantly expressed in canine OSA (see, e.g., Ferracini et al., *J Orthop Res* 18, 253-6 (2000); Ferracini et al., *Oncogene* 10, 739-49 (1995); Ferracini et al., *J Cell Physiol* 184, 191-6 (2000); and Scotlandi et al., *Am J Pathol* 149, 1209-19 (1996)).

The proto-oncogene Met was originally identified as the transforming gene of a human OSA cell line (MNNG-HOS) (Cooper et al. *Nature* 311, 29-33 (1984)). The ligand for Met is hepatocyte growth factor (HGF, also known as scatter factor) (Nakamura, *Prog Growth Factor Res* 3, 67-85 (1991); Nakamura et al., *Nature* 342, 440-3 (1989); Shimomura et al., *J Biol Chem* 268, 22927-32 (1993)). Met-HGF interactions promote an array of cellular responses such as proliferation, scattering (motility), and branching morphogenesis (Kan et al., *Biochem Biophys Res Commun* 174, 331-7 (1991); Montesano et al., *Cell* 67, 901-8 (1991); Weidner et al., *J Cell Biol* 111, 2097-108 (1990); Grant et al., *PNAS USA* 90, 1937-41 (1993); Birchmeier and Gherardi, *Trends Cell Biol* 8, 404-10 (1998)). Binding of HGF to Met initiates receptor dimerization and autophosphorylation at multiple tyrosine residues, resulting in a cascade of downstream signaling events including phosphorylation of adaptor proteins (Gab-1, Grb2, Shc, c-Cb1) and activation of PI3K, ERK1/2, FAK and PLCγ (Jiang et al., *Crit Rev Oncol Hematol* 29, 209-48 (1999); Maulik et al., *Cytokine Growth Factor Rev* 13, 41-59 (2002)). These signals are important in mediating a wide range of biological activities, including embryological development, wound healing, tissue regeneration, angiogenesis, invasion, and morphogenic differentiation (Jiang et al., *Crit Rev Oncol Hematol* 29, 209-48 (1999); Maulik et al., *Cytokine Growth Factor Rev* 13, 41-59 (2002); Birchmeier and Gherardi, *Trends Cell Biol* 8, 404-10 (1998)).

Increasing evidence suggests that both Met and HGF are dysregulated in a variety of canine, murine, and human cancers through mutation, overexpression, or co-expression of Met and HGF (Birchmeier et al., *Nat Rev Mol Cell Biol* 4, 915-25 (2003); Jeffers et al., *Proc Natl Acad Sci USA* 94, 11445-50 (1997); Jeffers et al., *Mol Cell Biol* 16, 1115-25 (1996); Jeffers et al., *Oncogene* 13, 853-6 (1996); Jeffers et al., *PNAS USA* 95, 14417-22 (1998); Pennacchietti et al., *Cancer Cell* 3, 347-61 (2003); Scarpino et al., *J Pathol* 202, 352-8 (2004); Schmidt et al., *Cancer Res* 58, 1719-22 (1998); Schmidt et al., *Nat Genet* 16, 68-73 (1997); Ma et al., *Cancer Res* 63, 6272-81 (2003); Lindor et al., *Genet Test* 5, 101-6 (2001); Lee et al., *Oncogene* 19, 4947-53 (2000); Di Renzo et al., *Oncogene* 19, 1547-55 (2000); Park et al., *Cancer Res* 59, 307-10 (1999); Ferracini et al., *Oncogene* 10, 739-49 (1995); Ferracini et al., *J Cell Physiol* 184, 191-6 (2000); Scotlandi et al., *Am J Pathol* 149, 1209-19 (1996); Tsao et al., *Lung Cancer* 20, 1-16 (1998); Ruco et al., *J Pathol* 180, 266-70 (1996); Ruco et al., *J Pathol* 194, 4-8 (2001)). It is also important to note that aberrant Met expression and/or function through mutation is associated with high tumor grade and a poor prognosis in a variety of human cancers (Di Renzo et al., *Clin Cancer Res* 1, 147-54 (1995); Baykal et al., *Gynecol Oncol* 88, 123-9 (2003); Carneiro, F. and Sobrinho-Simoes, M., *Cancer* 88, 238-40 (2000); Nakajima et al., *Cancer* 85, 1894-902 (1999); Takeuchi et al., *Clin Cancer Res* 9, 1480-8 (2003); Di Renzo et al., *Oncogene* 7, 2549-53 (1992)). Together, this data suggests that inappropriate expression or function of Met contributes to both tumor development and tumor progression.

Met dysregulation has also been implicated in canine cancer, specifically osteosarcoma (OSA). OSA is the most common bone tumor in dogs, representing approximately 85% of all bone tumors (Withrow et al., *Clin Orthop*, 159-68 (1991); Withrow and MacEwen, Small animal clinical oncology, xvii, 736 (W.B. Saunders, Philadelphia, 2001)). Both large and giant breed dogs are at a higher risk for the development of OSA, with certain breeds such as Rottweilers and Irish Wolfhounds over-represented (Withrow et al., *Clin Orthop*, 159-68 (1991); Withrow and MacEwen, 2001, supra).

OSA is a very aggressive tumor, causing lysis of the affected bone leading to a progressive lameness. While less than 10% of dogs have radiographically detectable pulmonary metastases at the time of presentation, over 90% have microscopic metastatic disease. Treatment involves removal of the primary tumor through either limb amputation or limb spare surgery. Amputation alone leads to a median survival time of 3-4 months, with nearly all dogs succumbing to metastasis within 1 year (Withrow et al., *Clin Orthop*, 159-68 (1991); Withrow. and MacEwen, 2001, supra). Survival times are extended to 8-12 months if adjuvant chemotherapy with cisplatin, adriamycin, or carboplatin is used (reviewed in (Withrow and MacEwen, 2001, supra); Chun and de Lorimier, *Vet Clin North Am Small Anim Pract* 33, 491-516, vi (2003))). However, less than 20% of patients will survive longer than 2 years. Recent efforts at co-administering adriamycin and a platinum compound have not improved survival times (Chun and de Lorimier, 2003, supra). In one report, 5 of 7 canine osteosarcoma (OSA) tumor samples exhibited high levels of Met expression as assessed by Northern analysis (Ferracini et al., *J Orthop Res* 18, 253-6 (2000)). In addition, a lung metastasis from one dog expressed Met at a higher level than the primary tumor. These results are similar to findings in human OSA in which 60%-95% of primary tumors and 80-100% of recurrences (local and distant) exhibit excessive Met expression (Ferracini et al., *Oncogene* 10, 739-49 (1995); Ferracini et al., *J Cell Physiol* 184, 191-6 (2000); Scotlandi et al., *Am J Pathol* 149, 1209-19 (1996)). Furthermore, Met was found to be overexpressed in multiple human OSA cell lines, and HGF stimulation induced phosphorylation, scattering and proliferation of these cells, although this effect varied in degree among the cell lines tested (Coltella et al., *Faseb J* 17, 1162-4 (2003)). Lastly, three canine OSA cell lines were recently demonstrated to express Met and to respond to HGF stimulation leading to Met phosphorylation (MacEwen et al., *Clin Exp Metastasis* 20, 421-30 (2003)).

Clearly, novel therapeutic approaches for the treatment of canine cancer are needed if significant improvements in clinical outcome are to occur.

It is therefore clear that there is a need in the art for more effective therapeutic and diagnostic approaches for treating and preventing canine cancers. The present invention addresses these and other needs.

BRIEF SUMMARY OF THE INVENTION

The present invention provides compositions and methods for detecting mutant Met sequences associated with cancer in canines.

One embodiment of the invention provides isolated polynucleotides comprising the sequence provided in SEQ ID NO:1, 2, or a complement thereof, expression vectors comprising a polynucleotide of claim 1, operably linked to an expression control sequence, and host cells (i.e. mammalian cells) comprising the expression vectors. The invention also provides isolated polypeptides comprising an amino acid sequence encoded by a SEQ ID NOS: 1 and 2. The invention also provides isolated nucleic acids comprising the sequence set forth in SEQ ID NOS: 3-6. The invention further provides isolated polypeptides comprising the amino acid sequence set forth in SEQ ID NO:7.

Another embodiment of the invention provides methods for detecting mutations associated with neoplasia in a canine by detecting a sequence comprising a G to A substitution at position 2896 of a gene encoding the Met receptor tyrosine kinase or a G to A substitution at position 1630 in a biological sample from the canine (e.g., a wild canine such as a wolf, a fox, or a coyote or a domesticated canine such as a Rottweiler, a Golden Retriever, a Boxer, a Sharpei, a Burmese Mountain Dog, a Flat-coated Retreiver, a Labrador Retriever, an Irish Wolfhound, or an American Pit Bull Terrier). The mutant Met sequence may comprise SEQ ID NO:1, 2, or a complement thereof. In some embodiments, the mutant Met sequence is detected by specifically amplifying a nucleic acid comprising the sequence from a biological sample from the canine and detecting the amplified nucleic acids, thereby detecting the mutation. The Met sequence may be specifically amplified using primers comprising the sequences set forth in SEQ ID NOS: 3 and 4 or 5 and 6. The mutation may be detected by contacting the amplified nucleic acids with a restriction enzyme (e.g., Dde I) or by sequencing the amplified product.

A further embodiment of the invention provides isolated polynucleotides capable of distinguishing between the sequence provided in SEQ ID NO:1 or a complement thereof and a nucleic acid encoding a wild type Met receptor tyrosine kinase protein and isolated polynucleotides capable of distinguishing between the sequence provided in SEQ ID NO:2 or a complement thereof and a nucleic acid encoding a wild type Met receptor tyrosine kinase protein.

These and other embodiments of the invention are further illustrated by the detailed description that follows.

BRIEF DESCRIPTION OF THE DRAWINGS

FIG. 1 depicts an alignment of canine Met wild type (SEQ ID NO:8) and mutant G1630A (SEQ ID NO:2) nucleotide sequences.

FIG. 2 depicts an alignment of canine Met wild type (SEQ ID NO:9) and mutant D544N (SEQ ID NO:7) amino acid sequences.

FIG. 3 illustrates data from pyrosequencing to detect the D544N mutation.

DETAILED DESCRIPTION OF THE INVENTION

I. Introduction

The present invention is based on the identification of mutations in the canine Met gene that are associated with neoplasia in canines. More particularly, the invention is based on the identification of two different mutations in the canine Met proto-oncogene, one of which is present in 60-80% of Rottweillers, a breed predisposed to OSA. Without being bound by theory, we hypothesize that these mutations in Met result in a lower threshold for activation of Met, resulting in a predisposition to malignant transformation. We further hypothesize that both mutations will result in abnormally prolonged Met signal transduction in response to HGF stimulation, thereby contributing to malignant transformation.

Thus, the invention provides compositions comprising isolated polynucleotides encoding mutant Met sequences and polypeptides encoded by such polynucleotides. The invention further provides methods, and kits for identifying mutant Met sequences and canines that are at risk for cancer (i.e., carriers of the mutant Met). Mutant Met sequences as diagnostic and prognostic markers for neoplastic disease (e.g., to predict how aggressively metastatic a tumor may be). Cells transfected with the mutant Met sequences can be used in development of therapy for cancer, e.g. to screen for antineoplastic agents. Canines identified as carriers of the mutant Met can be used as models for study of neoplastic disease and development of therapy for such diseases. Canines identified as carriers of the mutant Met can also be removed from breeding populations to enhance the overall health of dog breeds, both domesticated and wild.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y.), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The terms "c-Met," and "Met," refer to both mutant and wild type receptor tyrosine kinase found in, inter alia, canines, mice, and humans. The mouse and human Met genes encode a 190 Kd receptor composed of two disulfide-linked chains, an extracellular 50 kd α-chain, and a transmembrane 145 kd β-chain which shows tyrosine kinase activity (Giordano et al., *Nature* 339, 155-6 (1989);

Gonzatti-Haces et al., *PNAS USA* 85, 21-5 (1988)). Both chains are derived from a 170 kd precursor that is glycosylated and cleaved to give the mature heterodimer (Giordano et al., *Nature* 339, 155-6 (1989)). Canine Met is 1382 amino acids in length and exhibits 88% homology with the human sequence and 87% homology with the murine sequence.

The terms "c-Met," "mutant c-Met," "Met,", and "mutant Met" also refer to nucleic acids comprising a sequence set forth in Genbank Accession No. AY543631 or SEQ ID NOS:1 or 2 or complements thereof and to polypeptides encoded by such sequences (i.e., a protein encoded by SEQ ID NO:1 or 2 or a polypeptide comprising the sequence set forth in SEQ ID NO:7). "c-Met," "mutant c-Met," "Met,", and "mutant Met" also refer to nucleic acids comprising a sequence that specifically hybridize under stringent hybridization conditions to a sequence set forth in Genbank Accession No. AY543631 or SEQ ID NOS:1 or 2 or complements thereof as well as nucleic acids having a sequence that has greater than about 95%, preferably greater than about 96%, 97%, 98%, 99%, or higher nucleotide sequence identity, preferably over a region of at least about 25, 50, 100, 200, 500, 1000, or more nucleotides, to a sequence set forth in Genbank Accession No. AY543631 or SEQ ID NOS:1 or 2 or a complement thereof. A Met polynucleotide or polypeptide sequence is typically from a mammal including, but not limited to, domestic dogs and wild dogs (e.g., any member of the family Canidae). Typically, the mammals are of the genus *Canis* such as, for example, *C. lupus, C. lupus familiaris, C. lupus dingo, C. lupus mogollonensis, C. lupus baileyi C. rufus, C. simensis*). The Met nucleic acids and Met proteins of the invention include both naturally occurring or recombinant molecules. Mutant Met sequences include, e.g., sequences that comprise a mutation associated with neoplasia including, e.g., nucleotide sequences comprising SEQ ID NOS: 1, 2 or complements thereof. Mutant Met sequences also include, e.g., amino acid sequences encoded by the sequence comprising SEQ ID NOS: 1, 2 or complements thereof.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated mutant Met nucleic acid is separated from open reading frames that flank the mutant Met gene and encode proteins other than mutant Met. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nuc. Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

"Amplifying" refers to submitting a solution to conditions sufficient to allow for amplification of a target polynucleotide i.e., a mutant Met sequence) if all of the components of the reaction are intact. Components of an amplification reaction include, e.g., primers, a polynucleotide template, polymerase, nucleotides, and the like.

The term "subsequence" refers to a sequence of nucleotides that are contiguous within a second sequence but does not include all of the nucleotides of the second sequence.

A "target" or "target sequence" refers to a single or double stranded polynucleotide sequence sought to be amplified in an amplification reaction. Two target sequences are different if they comprise non-identical polynucleotide sequences.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region such as the intracellular juxtamembrane domain of the Met gene or another region of SEQ ID NOS:1 or 2), when compared and aligned for maximum correspondence over a comparison window, or designated region as measured using one of the following sequence comparison algorithms or by manual alignment and visual inspection. Such sequences are then said to be "substantially identical."

This definition also refers to the complement of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to mutant Met nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *PNAS. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *PNAS USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *PNAS USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min.

The phrase "selectively associates with" refers to the ability of a nucleic acid to "selectively hybridize" with another as defined above, or the ability of an antibody to "selectively (or specifically) bind to a protein, as defined above.

"Biological sample" as used herein is a sample of biological tissue or fluid that is suspected of containing a nucleic acid encoding a mutant Met polypeptide. These samples can be tested by the methods described herein and include body fluids such as whole blood, serum, plasma, lymph fluids, and various external secretions of the respiratory, intestinal and genitourinary tracts, tears, saliva, milk, white blood cells, and the like; and tissue samples including tumor samples and bone samples. The samples may be fresh, frozen, ore preserved in a fixative such as paraffin. A biological sample is obtained from any mammal including, e.g., any species of the family Canis. Suitable Canis species include, e.g., wild canines such as, e.g., wolves, foxes, and coyotes, and domesticated canines such as, e.g., Rottweilers, Golden Retrievers, Boxers, Sharpeis, Burmese Mountain Dogs, Flat-coated Retreivers, Laborador Retrievers, Irish Wolfhounds, or American Pit Bull Terriers). A biological sample may be suspended or dissolved in liquid materials such as buffers, extractants, solvents and the like.

III. Nucleic Acids Encoding Mutant Met

A. General Recombinant DNA Methods

This invention relies on routine techniques in the field of recombinant genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Cloning Methods for the Isolation of Nucleotide Sequences Encoding Mutant Met In general, the nucleic acid sequences encoding mutant Met and related nucleic acid sequence homologues are cloned from cDNA and genomic DNA libraries or isolated using amplification techniques with oligonucleotide primers. For example, mutant Met sequences are typically isolated from nucleic acid (genomic or cDNA) libraries by hybridizing with a nucleic acid probe, the sequence of which can be derived from SEQ ID NO:1, or a subsequence thereof. Mutant Met RNA and genomic DNA can be isolated from any canine including a dog such as, e.g., a Rottweiler or a Golden Retreiver. Methods for making and screening cDNA libraries and genomic DNA libraries are well known (see, e.g., Gubler & Hoffman, Gene 25:263-269 (1983); Sambrook et al., supra; Ausubel et al., supra; Benton & Davis, *Science* 196:180-182 (1977); and Grunstein et al., *PNAS USA,* 72:3961-3965 (1975)).

Nucleic acids encoding mutant Met can also be isolated from expression libraries using antibodies as probes. Such polyclonal or monoclonal antibodies can be raised using, for example, the polypeptides encoded by the sequence of SEQ ID NOS:1 or 2.

Mutant Met polymorphic variants, alleles, and interspecies homologues that are substantially identical to mutant Met can be isolated using mutant Met nucleic acid probes and oligonucleotides under stringent hybridization conditions, by screening libraries. Alternatively, expression libraries can be used to clone mutant Met polymorphic variants, alleles, and interspecies homologues, by detecting expressed homologues immunologically with antisera or purified antibodies made against the core domain of mutant Met which also recognize and selectively bind to the mutant Met homologue.

An alternative method of isolating mutant Met nucleic acids and their homologues combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). The primers canbe used, e.g., to amplify either the full length sequence or a probe of one to several hundred nucleotides, which is then used to screen a cDNA library for full-length mutant Met. For example, nucleic acids encoding mutant Met or fragments thereof may be obtained by amplification of a dog cDNA library or reverse transcribed from dog RNA using isolated nucleic acid primer pairs having the following sequences: 5' primer: 5' gcaatccacgagcccatgag 3' (SEQ ID NO:3) and 3' primer: 5' gtagttgggcttacacttcggg 3' (SEQ ID NO:4); or 5' primer: 5' gtcctgcagtcagtgtctctccg 3' (SEQ ID NO:5) and 3' primer: 5' ggtgcagctctcatttccaagg 3' (SEQ ID NO:6). Methods such as polymerase chain reaction (PCR) and ligase chain reaction (LCR) can be used to amplify nucleic acid sequences of mutant Met directly from mRNA, from cDNA, from genomic libraries or cDNA libraries. Degenerate oligonucleotides can be designed to amplify mutant Met homologues using the sequences provided herein. Restriction endonuclease sites can be incorporated into the primers. Polyinerase chain reaction or other in vitro amplification methods may also be useful, for example, to clone nucleic acid sequences that code for proteins to be expressed, to make nucleic acids to use as probes for detecting the presence of mutant Met encoding mRNA in physiological samples, for nucleic acid sequencing, or for other purposes. Genes amplified by the PCR reaction can be purified from agarose gels and cloned into an appropriate vector.

Gene expression of mutant Met can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

Synthetic oligonucleotides can be used to construct recombinant mutant Met genes for use as probes or for expression of protein. This method is performed using a series of overlapping oligonucleotides usually 40-120 bp in length, representing both the sense and non-sense strands of the gene. These DNA fragments are then annealed, ligated and cloned. Alternatively, amplification techniques can be used with precise primers to amplify a specific subsequence of the mutant Met gene. The specific subsequence is then ligated into an expression vector. mutant Met chimeras can be made, which combine, e.g., a portion of mutant Met with a portion of a heterologous mutant Met to create a chimeric, functional mutant Met.

C. Expression of Mutant Met in Recombinant Cells

To obtain high level expression of a cloned gene, such as those cDNAs encoding mutant Met, one typically subclones a mutant Met sequence (i.e., SEQ ID NOS:1 or 2 or a subsequence thereof) into an expression vector that is subsequently transfected into a mammalian cells. The expression vector typically contains a strong promoter or a promoter/enhancer to direct transcription, a transcription/translation terminator, and for a nucleic acid encoding a protein, a ribosome binding site for translational initiation. The promoter is perably linked to the nucleic acid sequence encoding mutant Met (e.g., SEQ ID NOS:1 or 2 or a subsequence thereof). Eukaryotic expression systems for mammalian cells are well known in the art and described, e.g., in Sambrook et al. and Ausubel et al. and are also commercially available. Preferably the mammalian cells are cells that do not endogenously express Met, HGF, or combinations thereof. Particularly preferred cells include, for example, MBCK cells, NIH 3T3 cells, or Jurkat cells.

The particular expression vector used to transport the genetic information into the cell is not particularly critical. Any of the conventional vectors used for expression in eukaryotic cells may be used. Preferred vectors include vectors that comprise a strong promoter/enhancer region such as, e.g., pCI-neo, or vectors that comprise multiple cloning sites followed by an internal ribosome entry site (IRES) and/or a sequence encoding a marker protein such as, e.g., pIRES2-EGFP. The vectors also typically comprise a gene encoding antibiotic resistance to permit selection of cells have been transformed with the vector. The particular antibiotic resistance gene chosen is not critical, any of the many resistance genes known in the art are suitable. Preferably the antibiotic resistance gene confers resistance to neomycin.

Standard transfection methods are used to produce cell lines that express large quantities of mutant Met protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of cells is performed according to standard techniques (see, e.g., Morrison, J. Bact. 132:349-351 (1977); Clark-Curtiss & Curtiss, Methods in Enzymology 101:347-362 (Wu et al., eds, 1983). For example, any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing mutant Met.

After the expression vector is introduced into the cells, the transfected cells are cultured under conditions favoring expression of mutant Met. The transfected cells are then used in functional assays (i.e., signal transduction assays, cell scattering and migration assays, and focus formation assays) to analyze the functional biological consequences of the particular mutant Met. Mutant Met can also be recovered from the culture using standard techniques identified below.

D. Purification of Mutant Met Protein

Either naturally occurring or recombinant mutant Met (i.e., Met encoded by the sequence set forth in SEQ ID NOS:1 OR 2) can be purified for use in functional assay. Naturally occurring mutant Met is purified, e.g., from a biological sample from a canine or any other source of a mutant Met homologue. Recombinant mutant Met can also be purified from any suitable expression system as described herein.

Once expressed, mutant Met may be purified to substantial purity by standard techniques known in the art, including, for example, size differential filtration, solubility fractionation, selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when recombinant mutant Met is being purified. For example, proteins having established molecular adhesion properties can be reversible fused to mutant Met. With the appropriate ligand, mutant Met can be selectively adsorbed to a purification column and then freed from the column in a relatively pure form. The fused protein is then removed by enzymatic activity. Finally mutant Met could be purified using immunoaffinity columns.

IV. Detection of Mutant Met Nucleic Acid Sequences

Canine can be tested to determine whether they are carriers of mutant Met, i.e., whether they are homozygous or heterozygous for mutant Met. Determination of the presence of absence of a particular mutant Met gene in the canine is generally performed by analyzing a nucleic acid sample that is obtained from a canine (e.g., a mammal of the genus canis) to be analyzed. Often, the nucleic acid sample comprises genomic DNA. It is also possible to analyze RNA samples for the presence of the Met mutations described herein.

Detection techniques for evaluating nucleic acids for the presence of a single base change involve procedures well known in the field of molecular genetics. Further, many of the methods involve amplification of nucleic acids. Ample guidance for performing the methods is provided in the art. Exemplary references include manuals such as PCR Technology: PRINCIPLES AND APPLICATIONS FOR DNA AMPLIFICATION (ed. H. A. Erlich, Freeman Press, NY, N.Y., 1992); PCR PROTOCOLS: A GUIDE TO METHODS AND APPLICATIONS (eds. Innis, et al., Academic Press, San Diego, Calif., 1990); CURRENT PROTOCOLS IN MOLECULAR BIOLOGY, Ausubel, 1994-1999, including supplemental updates through April 2004; Sambrook & Russell, *Molecular Cloning, A Laboratory Manual* (3rd Ed, 2001).

Although the methods typically employ PCR steps, other amplification protocols may also be used. Suitable amplification methods include ligase chain reaction (see, e.g., Wu & Wallace, *Genomics* 4:560-569, 1988); strand displacement assay (see, e.g., Walker et al., *PNAS USA* 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *PNAS USA* 86:1173-1177, 1989); and self-sustained sequence replication (3SR) (Guatelli et al., *PNAS USA* 87:1874-1878, 1990; WO 92/08800). Alternatively, methods that amplify the probe to detectable levels can be used, such as Qβ-replicase amplification (Kramer & Lizardi, *Nature* 339:401-402, 1989; Lomeli et al., *Clin. Chem.* 35:1826-1831, 1989). A review of known amplification methods is provided, for example, by Abramson and Myers in *Curr. Op. Biotech.* 4:41-47, 1993.

A. PCR

PCR can be used to detect carriers of mutant Met by amplification of nucleic acids encoding mutant Met. A general overview of the applicable technology can be found in PCR Protocols: A Guide to Methods and Applications (Innis et al. eds. (1990)) and PCR Technology: Principles and Applications for DNA Amplification (Erlich, ed. (1992)). In addition, amplification technology is described in U.S. Pat. Nos. 4,683,195 and 4,683,202.

PCR permits the copying, and resultant amplification of a target nucleic acid, e.g., a nucleic acid encoding mutant Met. In general, PCR and other methods of amplification use primers which anneal to either end of the DNA of interest. For example, nucleic acids encoding mutant Met or fragments thereof may be amplified using an isolated nucleic acid primer pair having the following sequences: 5' primer: 5' gcaatccacgagcccatgag 3' (SEQ ID NO:3) and 3' primer: 5' gtagttgggcttacacttcggg 3' (SEQ ID NO:4); or 5' primer: 5' gtcctgcagtcagtgtctctccg 3' (SEQ ID NO:5) and 3' primer: 5' ggtgcagctctcatttccaagg 3' (SEQ ID NO:6). Amplification of DNA encoding mutant Met from a biological sample from a subject (i.e., a canine) suspected of being a mutant Met carrier indicates that the subject is a carrier for mutant Met.

Target nucleic acid sequences may be double or single-stranded DNA or RNA from any biological sample from a canine suspected of being a carrier of mutant Met. Preferably, the target template is an isolated DNA sequence. Target DNA sequences may be isolated using a variety of techniques. For example, methods are known for lysing organisms and preparing extracts or purifying DNA. See, Current Protocols in Molecular Biology Volumes 1-3, John Wiley & Sons, Inc. (Ausubel et al., eds., 1994-1998) (hereinafter "Ausubel et al."). Also, total RNA or polyA+ RNA can be reverse transcribed to produce cDNA that can serve as the target DNA.

Typical PCR reaction components include, e.g., a target sequence, oligonucleotide primers, oligonucleotide probes, buffers (e.g., borate, phosphate, carbonate, barbital, Tris, etc. based buffers), salts (e.g., NaCl or KCl), a source of magnesium ions, dNTP's, and a nucleic acid polymerase (e.g., Taq DNA polymerase). PCR reactions can also include additional agents such as DMSO and stabilizing agents (e.g., gelatin, bovine serum albumin, and non-ionic detergents (e.g. Tween-20)).

The oligonucleotides (i.e., primers and probes) can be prepared by any suitable method, including chemical synthesis. Alternatively, they can be purchased through commercial sources. Methods of synthesizing oligonucleotides are well known in the art (see, e.g, Narang et al., *Meth. Enzymol.* 68:90-99, 1979; Brown et al., *Meth. Enzymol.* 68:109-151, 1979; Beaucage et al., *Tetrahedron Lett.* 22:1859-1862, 1981; and the solid support method of U.S. Pat. No. 4,458,066). These oligonucleotides can be labeled with radioisotopes, chemiluminescent moieties, or fluorescent moieties. Such labels are useful for the characterization and detection of amplification products using the methods and compositions of the present invention.

The primer are typically about 15 to about 60 nucleotides in length and are typically present in the PCR reaction mixture at a concentration of between about 0.1 and about 1.0 µM or about about 0.1 to about 0.75 µM. Typically the magnesium ion is present at about a 0.5 to 2.5 mM excess over the concentration of deoxynucleotide triphosphates (dNTPs). dNTPs typically are added to the reaction to a final concentration of about 20 µM to about 300 µM. Typically, each of the four dNTPs (G, A, C, T) are present at equivalent concentrations. (See, Innis et al.).

A variety of DNA dependent polymerases are commercially available that will function using the methods and compositions of the present invention. For example, Taq DNA Polymerase may be used to amplify the mutant Met sequences. Taq DNA polymerase which may be the native enzyme purified from *Thermus aquaticus* and/or a genetically engineered form of the enzyme. Other commercially available polymerase enzymes include, e.g., Taq polymerases marketed by Promega or Pharmacia. Other examples of thermostable DNA polymerases that could be used in the invention include DNA polymerases obtained from, e.g., *Thermus* and *Pyrococcus* species. Concentration ranges of the polymerase may range from 1-5 units per reaction mixture. The reaction mixture is typically between 20 and 100 µl.

One of skill in the art will recognize that buffer conditions, salt concentrations, magnesium ion concentrations, and dNTP concentrations can be designed to allow for the function of all reactions of interest, i.e., to support the amplification reaction as well as any subsequent restriction enzyme reactions. A particular set of reaction components can be tested for its ability to support various reactions by testing the components both individually and in combination. The optimal reaction conditions can vary depending on the nature of the target nucleic acid(s) and the primers being used, among other parameters.

B. Detection of Amplified Products

Amplified products can be detected using any means known in the art, including, e.g., restriction fragment length polymorphism (RFLP) analysis; denaturing gel electrophoresis, direct sequencing, and HPLC-based analysis, hybridization using sequence-specific oligonucleotides, primer extension, sequence-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. In addition to these frequently used methodologies for analysis of nucleic acid samples to detect single base changes, any method known in the art can be used to detect the presence of the mutant Met mutations described herein.

1. RFLP Analysis

In some embodiments, a mutant Met gene is detected using restriction fragment length polymorphism (RFLP) analysis. For example, Met is amplified from a biological sample from a canine suspected of having the Met mutation described herein (i.e., using primers comprising the sequence set forth in SEQ ID NO: 3 and 4). The amplification products of Met are digested with a restriction enzyme (e.g., Dde I) that digests the mutant Met, but not the wild type Met. The restriction fragments are then analyzed using gel electrophoresis. For example, dogs heterozygous for a mutant Met mutation associated with neoplasia have a 192 bp undigested wild type fragment and two digested fragments of 104 bp and 88 bp.

2. DNA Sequencing and Single Base Extensions

The mutant Met genes can also be detected by direct sequencing, e.g., to detect the G to A substitution at position 2896 of Met (i.e., the G966S mutation set forth in SEQ ID NO:1) and the G to A substitution at position 1630 (i.e., the D544N mutation set forth in SEQ ID NO:2) of Met. For example, Met is amplified from a biological sample from a canine suspected of having the Met mutation described herein (i.e., using primers comprising the sequence set forth in SEQ ID NO: 5 and 6) and the amplification product is sequenced. Suitable sequencing methods include e.g., dideoxy sequencing-based methods and Maxam and Gilbert sequence (see, e.g., Sambrook and Russell, supra).

Other detection methods include pyrosequencing of oligonucleotide-length products (see, e.g., Langaee et al., *Mutat Res.* 573(1-2):96-102 (2005); Diggle and Clarke, *Mol Biotechnol.* 28(2):129-37 (2004); Shi, *Am J Pharmacogenomics.* 2(3):197-205 (2002); Drmanac et al., *Eng Biotechnol.* 77:75-101 (2002); Franca et al., *Q Rev Biophys.* 35(2): 169-200 (2002); Fakhrai-Rad et al., *Hum Mutat.* 19(5):479-85 (2002); and Ronaghi et al., *Genome Res.* 11(1):3-11 (2001). Primers are typically used in conjunction with a labeled M 13 (e.g., biotin-labeled) primer to generate a pyrosequencing product for each sample under evaluation. A sequencing primer is hybridized to a single stranded, PCR amplified, DNA template (e.g., SEQ ID NO: 1 or 2), and incubated with the enzymes, DNA polymerase, ATP sulfurylase, luciferase and apyrase, and the substrates, adenosine 5' phosphosulfate (APS) and luciferin. The first of four deoxynucleotide triphosphates (dNTP) is added to the reaction. DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a pyrogram™. Each light signal is proportional to the number of nucleotides incorporated. Apyrase, a nucleotide degrading enzyme, continuously degrades unincorporated dNTPs and excess ATP. When degradation is complete, another dNTP is added. Addition of dNTPs is performed one at a time. Deoxyadenosine alpha-thio triphosphate (dATPαS) is typically used as a substitute for the natural deoxyadenosine triphosphate (dATP) since it is efficiently used by the DNA polymerase, but not recognized by the luciferase. As the process continues, the complementary DNA strand is built up and the nucleotide sequence is determined from the signal peak in the pyrogram.

The following primers and probe can be used to assess samples for the D544N mutation in cMET exon 4: forward (CACCAGGATCCCACTGAA; SEQ ID NO:10); reverse (TTGCAGGCAGACAGACCT; SEQ ID NO:11); and probe (CCAGGTGCACACATCTAT; SEQ ID NO:12). An M13 specific leader sequence (AGCGCATAACAATTTCACA-CAGG; SEQ ID NO:13) can be added to the 5' end of the forward primer.

Another similar method for characterizing single base changes does not require use of a complete PCR, but typically uses only the extension of a primer by a single, fluorescence-labeled dideoxyribonucleic acid molecule (ddNTP) that is complementary to the nucleotide to be investigated. The nucleotide at the site of the mutant Met mutation can be identified via detection of a primer that has been extended by one base and is fluorescently labeled (e.g., Kobayashi et al, *Mol. Cell. Probes,* 9:175-182, 1995).

3. HPLC

Target mutant Met sequences can be differentiated using high performance liquid chromatography (HPLC) based methods including denaturing HPLC (dHPLC) as described in e.g., Premstaller and Oefner, *LC-GC Europe* 1-9 (July 2002); Bennet et al., *BMC Genetics* 2:17 (2001); Schrimi et al., *Biotechniques* 28(4):740 (2000); and Nairz et al., *PNAS USA* 99(16):10575-10580 (2002); and ion-pair reversed phase HPLC-electrospray ionization mass spectrometry (ICEMS) as described in e.g., Oberacher et al.; *Hum. Mutat.* 21(1):86 (2003).

Partially denaturing HPLC analysis compares two or more sets of amplified products (e.g., a wild-type Met amplicon and a mutant Met amplicon). The amplified products are denatured (e.g., at about 95° C.) and allowed to reanneal by gradually lowering the temperature from about 95° C. to about 30° C. In the presence of a Met mutation the original homoduplex products are reformed along with heteroduplex products comprising the sense and anti-sense strands of either homoduplex. The homoduplexes and heteroduplexes are loaded onto an HPLC apparatus at a partially denaturing temperature of about 50° C. to about 70° C. and can be distinguished based on their elution profile. Completely denaturing HPLC analysis compares two or more sets of amplicons (e.g., primer extension products). The amplified products are loaded onto an HPLC apparatus at a completely denaturing temperature of about 70° C. to about 80° C. Specific sequence variants are eluted from the column by varying the temperature of the column and sequence variants are distinguished based on their order of elution from the column.

Ion-pair reversed phase HPLC-electrospray ionization mass spectrometry (ICEMS) uses a combination of HPLC under completely denaturing conditions and ICEMS to resolve differences between nucleic acid sequences.

4. Denaturing Gradient Gel Electrophoresis

Amplification products generated using the polymerase chain reaction can be analyzed by the use of denaturing gradient gel electrophoresis. Different Met mutations can be identified based on the different sequence-dependent melting properties and electrophoretic migration of DNA in solution (see, e.g., Erlich, ed., PCR TECHNOLOGY, PRINCIPLES AND APPLICATIONS FOR DNA AMPLIFICATION, W. H. Freeman and Co, New York, 1992, Chapter 7).

5. Single-Strand Conformation Polymorphism Analysis

Target mutant Met sequences can also be differentiated using single-strand conformation polymorphism analysis, which identifies base differences by alteration in electrophoretic migration of single stranded PCR products, as described, e.g, in Orita et al., *PNAS USA.* 86, 2766-2770 (1989). Amplified PCR products can be generated using methods known in the art, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between wild type and mutant Met sequences.

Methods for detecting single base changes often employ labeled oligonucleotides. Oligonucleotides can be labeled by incorporating a label detectable by spectroscopic, photochemical, biochemical, immunochemical, or chemical means. Useful labels include fluorescent dyes, radioactive labels, e.g., $^{32}P$, electron-dense reagents, enzyme, such as peroxidase or alkaline phsophatase, biotin, or haptens and proteins for which antisera or monoclonal antibodies are available. Labeling techniques are well known in the art (see, e.g., Current Protocols in Molecular Biology, supra; Sambrook & Russell, supra).

6. Sequence Specific Hybridization

A technique commonly referred to as allele specific oligonucleotide hybridization (ASO) (e.g., Stoneking et al., *Am. J. Hum. Genet.* 48:70-382, 1991; Saiki et al., *Nature* 324, 163-166, 1986; EP 235,726; and WO 89/11548) can used to detect mutant Met genes. Two DNA molecules differing by one base (e.g., wild type or mutant Met) are distinguished by hybridizing an oligonucleotide probe that is specific for one of the variants (e.g., wild type) to an amplified product obtained from amplifying the nucleic acid sample. The probes are designed to differentially hybridize to one variant versus another. The presence of a mutant Met mutation is determined by measuring the amount of sequence-specific oligonucleotide probe that is hybridized to the sample. Principles and guidance for designing such probes is available in the art (see, e.g., Jeffrys and Mays, *Genome Res.* 13(1): 2316-2324 (2003) and Howell et al., *Nature Biotech* 17(1): 87-88 (1999)). Hybridization conditions should be sufficiently stringent that there is a significant difference in hybridization intensity between alleles, and preferably an essentially binary response, whereby a probe hybridizes to only one of the sequences. Typically, the oligonucleotide probe is labeled with a label such as a fluorescent label. For example, a mutant Met-specific oligonucleotide is applied to immobilized oligonucleotides representing mutant Met sequences. After stringent hybridization and washing conditions, fluorescence intensity is measured for each mutant Met oligonucleotide.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; WO 95/11995 and WO 95/11995.

7. Sequence-Specific Amplification

Mutations are also commonly detected using sequence-specific amplification or primer extension methods. These reactions typically involve use of primers that are designed to specifically target a polymorphism via a mismatch at the 3' end of a primer. The presence of a mismatch effects the ability of a polymerase to extend a primer when the polymerase lacks error-correcting activity. For example, to detect a mutant Met sequence using a mutant Met-specific amplification- or extension-based method, a primer complementary to the wild type or mutant Met gene is designed such that the 3' terminal nucleotide hybridizes at the mutation site. The presence of the mutant Met mutation can be determined by the ability of the primer to initiate extension. If the 3' terminus is mismatched, the extension is impeded. Thus, for example, if a primer matches the mutant Met mutation at the 3' end, the primer matches and will be efficiently extended. Sequence-specific amplification- or extension-based methods are described in, for example, WO 93/22456; U.S. Pat. Nos. 5,137,806; 5,595,890; 5,639,611; and 4,851,331.

In an alternative probe-less method, the amplified nucleic acid is detected by monitoring the increase in the total amount of double-stranded DNA in the reaction mixture, is described, e.g., in U.S. Pat. No. 5,994,056; and European Patent Publication Nos. 487,218 and 512,334. The detection of double-stranded target DNA relies on the increased fluorescence various DNA-binding dyes, e.g., SYBR Green, exhibit when bound to double-stranded DNA.

As appreciated by one in the art, sequence-specific amplification methods, can be performed in reaction that employ multiple sequence-specific primers to target particular mutations. Primers for such multiplex applications are generally labeled with distinguishable labels or are selected such that the amplification products produced from the target sequences are distinguishable by size. Thus, for example, the presence of both a wild type and mutant Met gene in a single sample can be identified using a single amplification by gel analysis of the amplification product.

As in the case of sequence-specific probes, a sequence-specific oligonucleotide primer may be exactly complementary to one of the Met mutants in the hybridizing region or may have some mismatches at positions other than the 3' terminus of the oligonucleotide, which mismatches occur away from the site of the Met mutation. 5'-Nuclease Assay Genotyping can also be performed using a "TaqMan®" or "5'-nuclease assay", as described in U.S. Pat. Nos. 5,210,015; 5,487,972; and 5,804,375; and Holland et al., *PNAS USA* 88:7276-7280 (1988) or using a combined high-temperature reverse-transcription-polymerase chain reaction (RT-PCR), as described in U.S. Pat. Nos. 5,310,652; 5,322,770; 5,561,058; 5,641,864; and 5,693,517.

V. Immunological Detection of Mutant Met Polypeptides

In addition to the identification of carriers of mutant Met by detection of mutant Met nucleotides, Met polypeptides encoded by the sequence set forth in SEQ ID NOS:1 or 2 can be detected using immunoassays known in the art. For example, polyclonal or monoclonal antibodies that specifically bind to mutant Met, but not to wild-type Met can be used to detect mutant Met in a biological sample from a canine suspected of being a carrier of mutant Met. A general overview of the applicable technology can be found in Harlow & Lane, Antibodies: A Laboratory Manual (1988).

Methods of producing polyclonal and monoclonal antibodies that specifically bind mutant Met, or immunogenic fragments of mutant Met, are known to those of skill in the art (see, e.g., Coligan, Current Protocols in Immunology (1991); Harlow & Lane, supra; Goding, Monoclonal Antibodies: Principles and Practice (2d ed. 1986); Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)).

A number of immunogens comprising portions of mutant Met may be used to produce antibodies specifically reactive with mutant Met or homologues thereof. For example, recombinant mutant Met polypeptide (encoded by a sequence comprising SEQ ID NOS:1 or 2) or antigenic fragment thereof, can be isolated as described herein. Recombinant protein can be expressed in eukaryotic or prokaryotic cells as described above, and purified as generally described above for use as an immunogen. Alternatively, a synthetic peptide (e.g., PYPSLLSSQD-NIDGEGDT; SEQ ID NO:14) derived from the sequences disclosed herein and conjugated to a carrier protein can be used an iminunogen. Naturally occurring Met protein may also be used either in pure or impure form.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal and monoclonal antibodies and raised to mutant Met can be selected to obtain only those polyclonal and monoclonal antibodies that are specifically immunoreactive with mutant Met (e.g., a mutant Met encoded by the sequence set forth in SEQ ID NOS:1 or 2) and not with other proteins (e.g., wild type Met). This selection may be achieved by subtracting out antibodies that cross-react with molecules such as mutant Met from other species. In addition, polyclonal and monoclonal antibodies raised to mutant Met polymorphic variants, alleles, orthologs, and conservatively modified variants can be selected to obtain only those antibodies that recognize specific fragments of mutant Met. For example polyclonal antibodies raised to can be selected to obtain only those antibodies that recognize polypeptides encoded by a nucleic acid amplified by primers comprising the sequences set forth in SEQ ID NOS:3 and 4 or 5 and 6, but not other mutant Met fragments. A variety of immunoassay formats may be used to select antibodies specifically immunoreactive with a particular mutant Met. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective reaction will be at least twice background signal or noise and more typically more than 10 to 100 times background.

Immunoassays known in the art can be used to assess the binding specificity and binding affinity of antibodies that specifically bind to mutant Met. Typically, polyclonal antisera with a titer of $10^4$ or greater are selected and tested for their cross reactivity against non-mutant Met proteins, using a competitive binding immunoassay. Specific polyclonal antisera and monoclonal antibodies will usually bind with a Kd of at least about 0.1 mM, more usually at least about 1 μM, preferably at least about 0.1 μM or better, and most preferably, 0.01 μM or better. Antibodies specific only for a particular mutant Met homologue, such as the canine mutant Met encoded by a sequence comprising SEQ ID NOS:1 OR 2, can also be made, by subtracting out other cross-reacting homologues from a species such as a non-human mammal. For a review of immunological and immunoassay procedures, see Basic and Clinical Immunology (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra. For a review of the general immunoassays, see also Methods in Cell Biology: Antibodies in Cell Biology, volume 37 (Asai, ed. 1993); Basic and Clinical Immunology (Stites & Terr, eds., 7th ed. 1991). Immunoassays for detecting mutant Met or immunogenic fragments thereof in samples may be either competitive or noncompetitive. Noncompetitive immunoassays are assays in which the amount of antigen is directly measured. In competitive assays, the amount of the mutant Met present in the sample is measured indirectly by measuring the amount of known, added (exogenous) mutant Met displaced (competed away) from an anti-mutant Met antibody by the unknown mutant Met present in a sample. Western blot (immunoblot) analysis can also be used to detect and quantify the presence of the mutant Met polypeptides in the sample.

VI. Identification of Inhibitors of Met Signal Transduction

Inhibitors of Met signal transduction can be identified as potential therapeutic or diagnostic agents (e.g., as antineoplastic agents). Assays to measure Met signal transduction are well known in the art (see, e.g., Hov et al., *Clin Cancer Res.* 10(19):6686-94 (2004)). For example, cells transfected with wild-type or mutant canine Met can be used to identify compounds that inhibit Met signal transduction.

In certain embodiments, inhibitors of Met signal transduction can be identified using high throughput screening (HTS) methods. For example, combinatorial libraries of compounds can be screened for an ability to inhibit Met signal transduction. For example, peptides that antagonize binding of HGF to Met (see, e.g., WO 04/078778); trastuzumab, imatinib, bevacizumab, and gefitinib inhibitors (see, e.g., Christensen et al., *Cancer Lett.* 225(1):1-26 (2005)); or indolinones or their derivative (see, e.g., U.S. Pat. Nos. 6,855,730; 6,797,725; 6,777,417; 6,762,180; 6,716,870; 6,710,067; 6,706,709; 6,696,448; 6,689,806; 6,683,082; 6,653,308; 6,642,232; 6,638,965; 6,599,902; 6,579,897; 6,573,293; 6,545,035; 6,531,502; 6,486,185; 6,465,507; 6,451,838; 6,395,734; 6,350,754; 6,319,918; 6,316,429; 6,130,238; 6,114,371; 6,051,593; 4,882,329; 4,137,331; 4,053,613; 4,053,483; 4,020,179) may be screened for their ability to inhibit Met signal transduction. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Millions of chemical compounds can be synthesized through such combinatorial mixing of chemical building blocks (Gallop et al., *J. Med. Chem.* 37(9):1233-1251 (1994)).

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Pept. Prot. Res.* 37:487-493 (1991), Houghton et al., *Nature,* 354:84-88 (1991)), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., *PNAS USA* 90:6909-6913 (1993)), vinylogous polypeptides (Hagihara et al., *J. Amer. Chem. Soc.* 114:6568 (1992)), nonpeptidal peptidomimetics with a Beta-D-Glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho, et al., *Science* 261:1303 (1993)), and/or peptidyl phosphonates (Campbell et al., *J. Org. Chem.* 59:658 (1994)). See, generally, Gordon et al., *J. Med. Chem.* 37:1385 (1994), carbohydrate libraries (see, e.g., Liang et al., *Science* 274:1520-1522 (1996), and U.S. Pat. No. 5,593,853), and small organic molecule libraries including, for example libraries of indolinones (U.S. Pat. No. 6,147,106), benzodiazepines, (U.S. Pat. No. 5,288,514); isoprenoids (U.S. Pat. No. 5,569, 588); thiazolidinones and metathiazanones (U.S. Pat. No. 5,549,974); pyrrolidines (U.S. Pat. Nos. 5,525,735 and 5,519,134); and morpholino compounds (U.S. Pat. No. 5,506,337).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual synthetic operations performed by a chemist. The above devices, with appropriate modification, are suitable for use with the present invention. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

The assays to identify compounds that inhibit Met signal transduction are amenable to high throughput screening. High throughput assays for evaluating the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate procedures, including sample and reagent pipeting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

VII. Kits

The present invention also provides kits for detecting mutant Met nucleotides or peptides. Such kits typically comprise two or more components necessary for amplifying mutant Met nucleotides or for detecting mutant Met polypeptides. Components may be compounds, reagents, containers and/or equipment. In some embodiments, one container within a kit may contain a control Met sequence (e.g., a wild type Met sequence or SEQ ID NO:1 or 2) and another container within a kit may contain a set of primers, e.g., SEQ ID NOS: 3 and 4 and/or SEQ ID NOS: 5 and 6. Some kits may further comprise a restriction enzyme (e.g., Dde I) that digests a Met sequence amplified by the primers. In some embodiments, one container within a kit may contain a control Met polyeptpide and another container within a kit may contain a polyclonal or monoclonal antibody that specifically binds to mutant Met. In addition, the kits comprise instructions for use, i.e., instructions for using the primers in amplification and/or detection reactions as described herein or instructions for using the antibodies in immunoassays as described herein.

The kits may further comprise any of the extraction, amplification, detection reaction components or buffers described herein.

EXAMPLES

The following examples are provided to illustrate, but not to limit the claimed invention.

Example 1

Cloning of Met, HGF, and HGFA

We cloned canine Met, HGF and HGF activator (Genbank Accession Nos. AY543631, AY543632, AY532633, respectively), to develop reagents appropriate for RT-PCR, immunoprecipitation and Western blotting. Canine Met is 1382 amino acids in length and exhibits 88% homology with the human sequence and 87% homology with the murine sequence; HGF is 731 amino acids in length and exhibits 90% homology with the human sequence and 91% homology with the murine sequence; HGF activator is 655 amino acids in length and exhibits 81% homology with the human sequence and 74% homology with the murine sequence. We then evaluated the expression of Met and HGF mRNA in 4 canine OSA cell lines (OSCA2, OSCA8, OSCA11M and D17). All were found to express Met and HGF mRNA and all expressed HGFA mRNA with the exception of the D17 cell line.

Example 2

Identification of the Canine Met D544N Mutation

We next evaluated the phosphorylation status of Met in the OSA lines and determined if recombinant human HGF (rhHGF) was capable of eliciting an appropriate response. rhHGF induced phosphorylation of canine Met in all cell lines tested in a dose dependent fashion, with maximal stimulation occurring at 50 ng/ml. Interestingly, the D17 line exhibited a low level of basal phosphorylation in the absence of HGF stimulation. Subsequent evaluation of Met in this line demonstrated the presence of a point mutation in the extracellular domain leading to an amino acid change consisting of Asp544Asn (D544N). It is possible that this mutation results in the basal phosphorylation of Met in this cell line.

We next screened a number of additional canine tumor cell lines for the presence of the D544N mutation. The human osteosarcoma cell line, U2OS, was purchased from American Type Culture Collection (Manassas, Va.) and maintained in McCoy's 5 medium supplied with 10% fetal bovine serum, penicillin, streptomycin, and L-glutamine. Four canine osteosarcoma (OSA) cell lines, OSA2, OSA8, OSA11M and D17 and one hemangiosarcoma line, SB-HSA-2, were provided by Dr. Jaime Modiano (AMC Cancer Research Institute, Denver, Colo.). Three histiocytic sarcoma cell lines, Nike 1.1, 030210.4 and DH82, and the myeloid leukemia line, ML3, were provided by Dr. Peter Moore (School of Veterinary Medicine, UC Davis). Two mast cell tumor cell lines, C2 and BR, were provided by Dr. Warren Gold (Cardiovascular Research Institute, UCSF). The additional canine OSA cell lines 348617, 344706, 293069, 344886, 346092, 346381, 348529, and 344692 were provided by Dr. Bernard Seguin (School of Veterinary Medicine, UC Davis). The canine melanoma cell lines 321251, 322354, 323610, 325086, 326960, 326937, 344512, and 338301, were provided by Dr. Michael Kent (School of Veterinary Medicine, UC Davis). All canine cell lines were maintained in RPMI 1640 supplemented with 10% fetal bovine serum, non-essential amino acids, sodium pyruvate, HEPES, penicillin, streptomycin and L-glutamine. All cell lines tested expressed message for canine Met, including osteosarcomas, mast cell tumors, hemangiosarcoma, melanomas and histiocytic sarcomas. Additionally, 19 of the 25 lines tested expressed message for both HGF and HGFA indicating a potential role for autocrine Met stimulation in these cells.

To assess samples for the D544N mutation in cMET exon 4, a pyrosequencing assay was developed. Forward (CACCAGGATCCCACTGAA; SEQ ID NO:10) and reverse (TTGCAGGCAGACAGACCT; SEQ ID NO:11) primers were designed flanking the mutation of interest. An M13 specific leader sequence (AGCGCATAACAATTTCACACAGG; SEQ ID NO:13) was added to the 5' end of the forward primer. These primers were used in conjunction with a biotin labeled M13 primer to generate pyrosequencing product for each sample under evaluation. Using the pyrosequencing probe (CCAGGTGCACACATCTAT; SEQ ID NO:12), sample sequence was determined at the nucleotide position of interest. Homozygous wild type pyrosequencing data is shown in FIG. 3A. The heterozygous state is indicated in FIG. 3B while the homozygous affected state is depicted in FIG. 3C.

We also validated the ability of several phospho-Met specific antibodies to specifically bind canine Met. Specifically, we tested the anti-pY$^{1003}$, anti-pY$^{1349}$, anti-pY$^{1230/34/35}$, and anti-pY$^{1365}$, all from Biosource and found that each of these antibodies was capable of specifically binding (i.e., recognizing the specific phospho-motifs) to canine Met after rhHGF stimulation.

Example 3

Identification of the Canine Met G966S Mutation and Analysis of Mutation Incidence and Expression Patterns of Met in Canine OSA Samples We identified a mutation in the intracellular juxtamembrane domain in one of the OSA cell lines two canine OSA cell lines OSA11M and OSA2. This mutation is present in leads nucleotide substitution at position 2896 (G2896A), resulting in an amino acid change of glutamine to serine at position 966 (G966S) located in the juxtamembrane domain of Met, encoded by exon 14. The presence of the nucleotide change introduced a restriction cutting site for DdeI permitting rapid identification of the mutation through a simple PCR-restriction digest assay. Canine Met was used as a template to design a forward primer (gcaatccacgagcccatgag; SEQ ID NO:3) for use on genomic DNA, with the reverse primer (gtagttgggcttacacttcggg; SEQ ID NO:4) placed in the 3' end of exon 14. Following PCR, DdeI digest is performed and the products are then resolved on a 3.5% agarose gel by electrophoresis. Wild-type samples remain uncut, heterozygous samples demonstrate 3 distinct bands (192 bp uncut, 104 bp and 88 bp cut fragments), while homozygous samples demonstrate only the cut fragments.

We found that approximately 80% of Rottweillers carry this mutation, compared to less than 5% of all other breeds evaluated. These data suggest that dysfunction of Met may play a role in the predisposition of some dog breeds to the development of neoplasia. To confirm these results, we screened all of our available canine OSA cell lines for the G966S mutation. 7 of the 23 lines (30%) were found to be either heterozygous (n=6) or homozygous (n=1) for the G966S mutation. To confirm these results, of the PCR products were directly sequenced and the presence of the mutation was confirmed in all 7 samples. 6/7 cell lines were derived from Rottweillers, while the remaining line was derived from a mixed breed dog.

We next screened random genomic DNA from random dog blood samples obtained from the Veterinary Medical Teaching Hospital at UC Davis, as we reasoned that such samples would provide a reasonable pool of a variety of dog breeds. Of the 433 samples screened, 4.8% (21/433) were found to carry the G966S mutation. The positive samples were all confirmed by direct sequencing to be either heterozygous (n=15) or homozygous (n=6) for the mutation, thus confirming that the G966S change is indeed germline in nature, and not the consequence of a somatic change associated with tumorigenesis. 11/21 positive dogs were Rottweillers, and of the 10 that were not, 4 were Rottweiller mixes.

Based on the VMTH blood sample screening and the screening of OSA cell lines in which 22/28 samples possessing the mutation were derived from Rottweillers or Rottweiller mixes, we suspected that a high percentage of Rottweillers may be carrying the G966S change in their germline. To explore this possible connection, blood samples and/or genomic DNA were solicited from Rottweiller breeders as well as from Dr. Jaime Modiano (AMC Cancer Research Center) who had collected samples for a separate project. Rottweillers were screened for the G966S mutation as follows. Briefly, peripheral blood mononuclear cells were collected and the resultant genomic DNA was extracted using the DNeasy kit(Qiagen, Valencia, Calif.). PCR was performed using the primer pair sense 5' gcaatccacgagcccatgag3' (SEQ ID NO:3) and antisense 5'gtagttgggcttacacttcggg3' (SEQ ID NO:4) for 40 cycles (94° C. 30 sec, 60° C. 30 sec, 72° C. 90 sec). The intact PCR product was 192 bp in length; this was digested with DdeI and the digest products will be evaluated by agarose gel electrophoresis. Digestion of the mutant allele yields two products (104 bp and 88 bp) while the wild-type allele remains intact. 78% (68/87) of Rottweillers were found to carry the mutation. Within this population, 42 were heterozygous while 26 were homozygous for the mutation. Based on these results, Rottweillers appear to carry a germline mutation in Met and it is possible that this mutation may play a role in their high rates of cancer.

To directly evaluate tumor specimens for the presence of the G966S mutation, archived paraffin embedded OSA tumor specimens will be obtained. A survey of the VMTH pathology data base has revealed at least 100 available OSA specimens. Briefly, 25μ sections of tumor will be collected into microcentrifuge tubes, the paraffin will be removed using xylene, and genomic DNA will be obtained according to a previously established protocol (Downing et al., *Am J Vet Res* 63, 1718-1723 (2002)). PCR and restriction digestion analysis will be performed as described above. These experiments will determine whether dogs that do not carry the germ line G966S mutation develop this mutation during tumorigenesis.

Example 4

Response of OSA Cells to Stress and Hypoxia

As it recently has been demonstrated that stress and/or hypoxia can lead to upregulation of Met expression, we sought to evaluate the effects of such conditions on canine OSA cells in culture. To evaluate the ability of OSA cells to scatter and migrate, we cultured cells in medium containing fetal bovine serum or no fetal bovine serum (stressful condition), then stimulated with HGF. The OSA cells began to show evidence of morphology change (scattering) upon growth factor deprivation. This was further enhanced when HGF was added to the tissue culture medium, demonstrating that similar to human OSA cells, canine OSA cells respond to cell stress by scattering and migrating in the presence of HGF.

To evaluate the effects of hypoxia on Met gene expression, we cultured two different canine OSA cell lines in the presence of cobalt chloride, an agent that mimics hypoxia. Using semi-quantitative RT-PCR, it can be seen that the addition of cobalt chloride to the tissue culture medium leads to upregulation of Met gene expression. Together, these results demonstrate that the biological response of Met to stress and hypoxia in canine tumor cells is similar to that found in human cancer cells. Given the substantial data indicating a role of Met in a variety of human cancers, it is likely that dysregulation of Met will play a similar role in canine cancers.

Example 5

D544N Mutation Incidence and Expression patterns of Met in Canine OSA Samples

To screen for the D544N mutation, we will use the genomic DNA isolated from the peripheral blood and tumor specimens detailed above. We have developed a pyrosequencing assay (see FIG. 1) that is capable of detecting the point mutation. We will use this asay to first evaluate the tumor specimens to determine whether any evidence of the D544N change exists. Should no tumors be found to possess this mutation, then only a limited number of peripheral blood samples will be analyzed for evidence of a germ line mutation.

To determine the relationship of Met expression in primary OSA tumor samples to tumor behavior, we have generated an anti-canine Met antibody, i.e., a rabbit polyclonal anti-Met antibody directed against the carboxy terminus of canine Met (peptide sequence PYPSLLSSQDNIDGEGDT; SEQ ID NO:14). Once the antibody has been verified to work appropriately in formalin fixed pellets made from the D17 canine OSA line, we will analyze the expression of Met on canine OSA tumor samples. Briefly, paraffin sections will be boiled at 95° C. for 5 minutes in the Dako Antigen Retrieval Solution (DakoCytomation, Carpinteria, Calif.), to unmask antigen and routine immunohistochemical (IHC) analysis will be performed for Met using the Biosource antibody and the Vectastain ABC Kit (Vector Labs, Burlingame, Calif.). The D17 cell pellet will be used as the positive control, and pooled normal rabbit IgG will be used for the negative control. Additionally, we will use the Met peptide (provided by Biosource) to block staining to demonstrate specificity of the reaction. To determine the relationship between Met expression and overall survival, the OSA samples will be scored for positive staining on a scale of 0-5 (0=no positive cells) and a breakpoint between high and low Met staining will be identified. The survival distribution will be plotted using the method of Kaplan and Meier and the log-rank test will be used to determine if there is a significant difference. Data analyses will be performed using commercial statistical software (StatView, SAS Institute, Inc). A p-value <0.05 will be used to indicate statistical significance.

Example 6

Effect of Met Mutations on Met Signal Transduction

6A. Studies Using Canine Cell Lines

To determine whether HGF stimulation of canine Met induces appropriate Met autophosphorylation and downstream signal transduction, Met expressing tumor cell lines were treated with recombinant human HGF and the phosphorylation of Met on several specific tyrosines as well as phosphorylation of downstream signaling components were evaluated. FIG. 1a demonstrates Met phosphorylation in canine OSA and melanoma cell lines after rhHGF stimulation. It was then necessary to determine whether all critical tyrosine residues were phosphorylated after rhHGF exposure, as it was possible that the recombinant human protein was only inducing partial or incomplete signal transduction. Using the OSA8 canine OSA cell line, it was determined that tyrosines 1003, 1230/34/35, 1349, and 1365 were all phosphorylated appropriately. The D17 canine OSA cell line showed basal levels of Met phosphorylation even after 24 hours of serum starvation. Although this could be attributed to autocrine HGF and HGFA production, the D17 cell line also has the D544N mutation.

The activation of downstream signal transduction components Gab-1, Erk1/2, and Akt were then examined. In each of the canine cell lines tested, Gab-1 was phosphorylated after stimulation of cells with rhHGF. The D17 cell line showed basal phosphorylation of Gab-1 in the absence of HGF stimulation. Not all cell lines evaluated demonstrated an apparent correlation of rhHGF stimulation with phosphorylation of Erk1/2; some of these showed high basal phosphorylation even in the face of 12 hours of serum starvation. Levels of Akt phosphorylation also did not appear to change substantially after rhHGF stimulation in some of the cell lines. It is possible that in these cases, other growth factor pathways contribute to this high level of basal phosphorylation. However, some of the other cell lines evaluated (Mel 3 and Mel 8) demonstrated inducible Erk and Akt phosphorylation upon rhHGF stimulation.

6B. Studies Using Cell Lines Stably Transfected with Canine Met Constructs

The following studies will analyze Met signal transduction clarify the biochemical consequences of each mutation and provide a framework for potential therapeutic intervention. As previously discussed, recent evidence suggests that mutations in Met do not lead to constitutive activation of the receptor but instead result in a lower threshold for activation and prolonged signal transduction by preventing c-cbl induced Met ubiquitination and subsequent degradation (Lee et al., *Oncogene* 19, 4947-53 (2000); Chiara et al., *J Biol Chem* 278, 29352-8 (2003)). To investigate the functional consequences of mutant canine Met, we stably transfected the full length cDNAs containing these mutations into suitable cell lines that do not express HGF or Met. The full length products will be generated from the following tissues: wild-type canine Met from normal canine liver, D544N mutant from the D17 canine OSA cells (ATCC), and G966S mutant from the OSCA 8 canine OSA cell line (provided by Dr. Jaime Modiano). To generate the known human R9886, P1009S, and M1251T Met mutants on the canine Met background, we emplyed site-directed mutagenesis of wild-type canine Met using the QuikChange XL mutagenesis kit (Stratagene, La Jolla, Calif.). The human Met mutants serve as a reference for changes in both Met signal transduction and Met biological responses as all of these mutations are known to alter Met signal transduction and Met induced migration/scattering. The following primers were used to generate wild-type canine Met from normal canine liver: ATGAAGGCTCCTGCTGTGCTTGCACCTG-GCATCCTTG (SEQ ID NO:15) (forward) and gggaccaaTCATGTGTCCCCTCGCCATCAATGTTATCTTGTG (SEQ ID NO:16) (reverse).

Once the constructs were generated by RT-PCR, they were subcloned into the pIRES2-EGFP vector (Clonetech) that possesses a neomycin resistance gene for selection of transfectants and a strong CMV enhancer/promoter region.

The stably transfected cells will be used in studies to assess the effect of the mutations on Met signal transduction including downstream signaling molecules: Gab-1, Erk1/2, and Akt. Furthermore, these stable transfectants will be used to study the biological effects of the mutations on cell migration and scattering.

We have screened a number of cell lines for Met and HGF expression and have found that Jurkat cells do not express Met or HGF, while NIH3T3 and MDCK (canine kidney) cells both express Met but not HGF. To prevent confounding signal transduction results due to the expression of wild-type Met, the constructs generated in the section above will be stably transfected into Jurkat cells. Approximately $10 \times 10^6$ cells will be serum starved overnight then either left untreated or exposed to 5 ng/ml (sub-optimal) or 50 ng/ml (optimal) rhHGF for 15 minutes. Cells will then be collected, lysed in protein lysis buffer containing both protease and phosphatase inhibitors, and Met will be immunoprecipitated using the anti-mouse Met polyclonal rabbit antibody (Upstate) or the anti-canine Met polyclonal rabbit antibody (made by Biosource). After SDS polyacrylamide gel electrophoresis (PAGE) of the immunoprecipitates, Western blotting will be performed using the previously validated phospho-specific Met antibodies (anti-pY$^{1003}$, anti-pY$^{1349}$, anti-pY$^{1230/34/35}$, and anti-pY$^{1365}$) to directly assess the phosphorylation state of the Met mutants in the presence or absence of HGF. The blots will then be stripped and re-probed for total Met. These experiments will provide information regarding whether either of the canine Met mutants possess baseline autophosphorylation in the absence of HGF stimulation and whether the threshold for phosphorylation of Met has been lowered by the presence of either mutation. To determine if either of the canine Met mutations results in extended Met phosphorylation upon stimulation, we will perform the same experiment as detailed above but instead of collecting the cells 15 minutes after stimulation, cells will be washed out of HGF, re-plated in medium lacking FBS, and collected at 6, 12, and 24 hours.

In addition to the studies described above, we will also evaluate the effect of Met mutations on three specific downstream signaling molecules: Gab-1, a major adaptor molecule for Met that is phosphorylated after HGF stimulation; Erk1/2, members of the MAPK signaling pathway that are important mediators of cell growth and survival for growth factor receptors; and Akt, a downstream target of P13-kinase that is phosphorylated upon growth factor binding. These pathways all play a role in HGF mediated Met signaling and it is possible that the canine Met mutations alter their function (Birchmeier et al., *Nat Rev Mol Cell Biol* 4, 915-25 (2003)). Approximately $10 \times 10^6$ stably transfected Jurkat cells will be serum starved overnight then either left untreated or exposed to 5 ng/ml (sub-optimal) or 50 ng/ml (optimal) rhHGF for 15 minutes and collected immediately or at 2, 12, and 24 hours. After lysis, protein will be quantitated, SDS-PAGE will be performed, and Western blotting for phospho-Gab-1, Erk1/2, and Akt will be performed. The blots will be stripped and re-probed for total Gab-1, Erk1/2, and Akt (all antibodies from Cell Signaling Technology) to control for protein loading.

Example 7

Determine the Effects of Met Mutations on Cell Biology

To futher characterize the identified Met mutations, scattering and migration assays and focus formations assays can be performed.

7A. Effect of Met Mutations on Scattering and Migration

NIH-3T3 cells were stably transfected with constructs for wild-type canine Met, R988C canine Met, M1251T canine Met (both mimic human Met mutants that exhibits transforming activity and is found in human cancers) and the canine D544N and G966S Met mutants. Cells were allowed to grow to confluence in tissue culture, then defects were created manually to create a "gap" in the cells. The cells were then left in medium alone or treated with recombinant human HGF (rhHGF) at 50 ng/ml. Cells were also treated with a Met inhibitor in the absence or presence of rhHGF. Cultures were evaluated 24 hours later by staining the cells with crystal violet and digital imaging. The NIH-3T3 lines stably transfected with R988C, M1251T, D544N, and G966S Met all exhibited higher baseline levels of migration in the absence of rhHGF which was markedly increased in the presence of rhHGF when compared to NIH-3T3 expressing wild-type Met. Therefore, the canine D544N and G966S Met mutants exhibit greater migratory capacity than its wild type counterpart.

7B. Assess Tumorigenic Potential of Met Mutations

To determine whether the mutant forms of Met are likely to be tumorigenic, the stably transfected NIH3T3 cells will be cultured at low FBS concentrations in soft agar as previously described (Jeffers et al., *PNAS USA* 94, 11445-50 (1997); Lee et al., *Oncogene* 19, 4947-53 (2000)). Foci of transformed cells will be counted at 2, 4, and 6 weeks after staining with Giemsa dye. The P1009S and M1251T mutants are known to induce focus formation of NIH3T3 cells in the soft agar assay and will serve as a positive control (Jeffers et al., 1997, supra; Lee et al., 2000, supra).

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all Accession Nos., articles and references, including patent applications, patents and PCT publications, are incorporated herein by reference for all purposes.

What is claimed is:

1. A method for detecting a mutation associated with osteosarcoma in a Rottweiler, said method comprising
   (a) collecting a sample from the Rottweiler; and
   (b) detecting position 2896 of SEQ ID NO:1, wherein the presence of an A at position 2896 of SEQ ID NO:1 is indicative of a mutation associated with osteosarcoma in a Rottweiler.

2. The method of claim 1, wherein the sequence is detected by
   (a) specifically amplifying a nucleic acid comprising the sequence in the biological sample, thereby amplifying nucleic acids comprising the mutation; and
   (b) detecting the amplified nucleic acids, thereby detecting the mutation.

3. The method of claim 2, wherein the nucleic acids are specifically amplified using primers comprising the sequences set forth in SEQ ID NOS: 3 and 4.

4. The method of claim 2, wherein the mutation is detected by contacting the amplified nucleic acids with a restriction enzyme.

5. The method of claim 4, wherein the restriction enzyme is Dde I.

6. The method of claim 2, wherein the amplified nucleic acids are detected by sequencing.

* * * * *